(12) United States Patent
Saunier

(10) Patent No.: US 7,485,156 B2
(45) Date of Patent: *Feb. 3, 2009

(54) COMPOSITION FOR DYEING KERATIN FIBERS, COMPRISING AT LEAST ONE DIAMINO-N,N-DIHYDROPYRAZOLONE DERIVATIVE, AT LEAST ONE COUPLER AND AT LEAST ONE ASSOCIATIVE POLYURETHANE POLYMER

(75) Inventor: Jean-Baptiste Saunier, Paris (FR)

(73) Assignee: L'Oreal S.A., Paris (FR)

( * ) Notice: Subject to any disclaimer, the term of this patent is extended or adjusted under 35 U.S.C. 154(b) by 35 days.

This patent is subject to a terminal disclaimer.

(21) Appl. No.: 11/443,353

(22) Filed: May 31, 2006

(65) Prior Publication Data

US 2006/0277693 A1 Dec. 14, 2006

Related U.S. Application Data

(60) Provisional application No. 60/689,061, filed on Jun. 10, 2005.

(30) Foreign Application Priority Data

May 31, 2005 (FR) .................................. 05 51429

(51) Int. Cl.
*A61Q 5/10* (2006.01)
*C07D 231/44* (2006.01)
*A01N 43/56* (2006.01)

(52) U.S. Cl. ...................... 8/405; 8/406; 8/407; 8/408; 8/410; 8/411; 8/412; 8/421; 8/567; 514/406; 514/407; 548/369.1

(58) Field of Classification Search .................. 8/405, 8/406, 407, 408, 410, 411, 412, 421, 567; 514/406, 407; 548/369.1
See application file for complete search history.

(56) References Cited

U.S. PATENT DOCUMENTS

| | | | |
|---|---|---|---|
| 3,649,158 A | 3/1972 | Kalopissis | |
| 4,003,699 A | 1/1977 | Rose et al. | |
| 4,128,425 A | 12/1978 | Greenwald | |
| RE30,199 E | 1/1980 | Rose et al. | |
| 4,314,808 A | 2/1982 | Jacquet et al. | |
| 4,823,985 A | 4/1989 | Grollier et al. | |
| 5,061,289 A | 10/1991 | Clausen et al. | |
| 5,089,025 A | 2/1992 | Rose et al. | |
| 5,380,340 A | 1/1995 | Neunhoeffer et al. | |
| 5,534,267 A | 7/1996 | Neunhoeffer et al. | |
| 5,663,366 A | 9/1997 | Neunhoeffer et al. | |
| 5,708,151 A | 1/1998 | Möckli | |
| 5,752,984 A | 5/1998 | Knuebel et al. | |
| 5,766,576 A | 6/1998 | Löwe et al. | |
| 5,865,855 A | 2/1999 | Doehling et al. | |
| 5,931,973 A | 8/1999 | Malle et al. | |
| 6,022,379 A | 2/2000 | Genard et al. | |
| 6,099,592 A | 8/2000 | Vidal et al. | |
| 6,099,593 A | 8/2000 | Terranova et al. | |
| 6,284,003 B1 | 9/2001 | Rose et al. | |
| 6,338,741 B1 | 1/2002 | Vidal et al. | |
| 6,391,064 B1 | 5/2002 | Baudry et al. | |
| 6,407,260 B1 | 6/2002 | Bonaventure et al. | |
| 6,432,146 B1 | 8/2002 | Rondeau | |
| 6,464,731 B1 | 10/2002 | Genet et al. | |
| 6,645,258 B2 | 11/2003 | Vidal et al. | |
| 6,692,538 B2 | 2/2004 | Bonaventure et al. | |
| 6,712,861 B2 | 3/2004 | Rondeau | |
| 6,730,789 B1 | 5/2004 | Birault et al. | |
| 6,773,463 B2 | 8/2004 | Pasquier et al. | |
| 6,884,265 B2 | 4/2005 | Vidal et al. | |
| 6,893,471 B2 | 5/2005 | Vidal | |
| 7,001,436 B2 | 2/2006 | Vidal et al. | |
| 7,285,137 B2 * | 10/2007 | Vidal et al. | ..................... 8/405 |
| 2001/0023514 A1 | 9/2001 | Cottard et al. | |
| 2003/0124079 A1 | 7/2003 | Mougin et al. | |
| 2003/0172475 A1 * | 9/2003 | Desenne et al. | ................. 8/408 |
| 2004/0060126 A1 | 4/2004 | Cottard et al. | |
| 2004/0141943 A1 | 7/2004 | Mougin et al. | |
| 2004/0194228 A1 | 10/2004 | Lagrange | |
| 2004/0194229 A1 | 10/2004 | Lagrange | |
| 2004/0200009 A1 | 10/2004 | Vidal | |

(Continued)

FOREIGN PATENT DOCUMENTS

DE 16 17 893 6/1971

(Continued)

OTHER PUBLICATIONS

English Language Derwent Abstract for DE 101 18 271 (2002).
English Language Derwent Abstract for DE 101 48 847 (2003).
English Language Derwent Abstract for DE 201 04 441 (2002).
English Language Derwent Abstract for EP 0 770 375 (1997).
English Language Derwent Abstract for EP 1 197 203 (2002).
English Language Derwent Abstract for FR 2 456 764 (1980).
English Language Derwent Abstract for JP 2-19576 (1990).
English Language Derwent Abstract for JP 5-163124 (1993).
Co-pending U.S. Appl. No. 11/443,273, Title: Composition For Dyeing Keratin Fibers, Comprising a Diamino-N,N-Dihydropyrazolone Derivative, a Coupler and a Polyol Inventors: Jean-Baptiste Saunier U.S. Filing Date: May 31, 2006.

(Continued)

*Primary Examiner*—Eisa B Elhilo
(74) *Attorney, Agent, or Firm*—Finnegan, Henderson, Farabow, Garrett & Dunner LLP

(57) ABSTRACT

The present disclosure relates to a composition for dyeing keratin fibers, for example, human keratin fibers such as the hair, comprising at least one oxidation base chosen from diamino-N,N-dihydropyrazolone compounds and addition salts thereof, at least one coupler and at least one associative polyurethane polymer, and also to a dyeing process and kit using such a composition.

The present disclosure makes it possible, for instance, to obtain fast coloration of keratin fibers that is resistant to light and to washing.

41 Claims, No Drawings

U.S. PATENT DOCUMENTS

| | | |
|---|---|---|
| 2005/0000037 A1 | 1/2005 | Audousset |
| 2005/0008594 A1 | 1/2005 | Plos et al. |
| 2005/0039268 A1 | 2/2005 | Plos et al. |
| 2005/0060815 A1 | 3/2005 | Kravtchenko et al. |
| 2005/0076458 A1 | 4/2005 | Cottard et al. |
| 2005/0166335 A1 | 8/2005 | Vidal et al. |
| 2005/0183211 A1 | 8/2005 | Samain et al. |
| 2005/0204483 A1 | 9/2005 | Samain et al. |
| 2006/0070191 A1 | 4/2006 | Lang et al. |

FOREIGN PATENT DOCUMENTS

| | | |
|---|---|---|
| DE | 23 59 399 | 6/1975 |
| DE | 38 25 212 | 2/1990 |
| DE | 38 43 892 | 6/1990 |
| DE | 41 33 957 | 4/1993 |
| DE | 42 34 885 | 4/1994 |
| DE | 44 04 564 | 8/1995 |
| DE | 195 43 988 | 5/1997 |
| DE | 197 30 412 | 12/1998 |
| DE | 101 18 271 | 3/2002 |
| DE | 201 04 441 | 7/2002 |
| DE | 101 48 847 | 4/2003 |
| EP | 0 173 109 | 3/1986 |
| EP | 0 714 954 | 6/1996 |
| EP | 0 770 375 | 5/1997 |
| EP | 0 984 010 | 3/2000 |
| EP | 1 025 834 | 8/2000 |
| EP | 1 166 753 | 1/2002 |
| EP | 1 166 754 | 1/2002 |
| EP | 1 170 000 | 1/2002 |
| EP | 1 170 001 | 1/2002 |
| EP | 1 197 203 | 4/2002 |
| EP | 1 437 123 | 7/2004 |
| EP | 1 464 327 | 10/2004 |
| EP | 1 473 023 | 11/2004 |
| EP | 1 550 656 | 7/2005 |
| EP | 1 598 047 | 11/2005 |
| FR | 1 584 111 | 12/1969 |
| FR | 2 456 764 | 12/1980 |
| FR | 2 586 913 | 3/1987 |
| FR | 2 733 749 | 11/1996 |
| FR | 2 746 392 | 9/1997 |
| FR | 2 750 048 | 12/1997 |
| FR | 2 760 010 | 8/1998 |
| FR | 2 782 452 | 2/2000 |
| FR | 2 788 273 | 7/2000 |
| FR | 2 798 931 | 3/2001 |
| FR | 2 801 308 | 5/2001 |
| FR | 2 803 195 | 7/2001 |
| FR | 2 811 993 | 1/2002 |
| FR | 2 817 467 | 6/2002 |
| FR | 2 822 696 | 10/2002 |
| FR | 2 825 622 | 12/2002 |
| FR | 2 825 625 | 12/2002 |
| FR | 2 825 702 | 12/2002 |
| FR | 2 825 703 | 12/2002 |
| FR | 2 833 834 | 6/2003 |
| FR | 2 845 387 | 4/2004 |
| FR | 2 848 837 | 6/2004 |
| FR | 2 848 840 | 6/2004 |
| FR | 2 855 966 | 12/2004 |
| FR | 2 855 967 | 12/2004 |
| GB | 1 026 978 | 4/1966 |
| GB | 1 153 196 | 5/1969 |
| GB | 1 213 697 | 11/1970 |
| JP | 2- 19576 | 1/1990 |
| JP | 5-163124 | 6/1993 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |
| WO | WO 02/22093 | 3/2002 |

OTHER PUBLICATIONS

Co-pending U.S. Appl. No. 11/443,274, Title: Composition For Dyeing Keratin Fibers, Comprising at least one Diamino-N,N-Dihydropyrazolone Derivative, at least one Coupler, and at Least One Surfactant Inventors: Jean-Baptiste Saunier U.S. Filing Date: May 31, 2006.

Co-pending U.S. Appl. No. 11/442,967, Title: Composition For Dyeing Keratin Fibers, Comprising at Least One Diamino-N,N-Dihydropyrazolone Derivative, at Least One Coupler, and at Least One Heterocyclic Direct Dye Inventors: Leila Hercouet U.S. Filing Date: May 31, 2006.

European Search Report for EP 06 11 4654, mailed Aug. 23, 2006 (corresponding to U.S. Appl. No. 11/443,273).

European Search Report for EP 06 11 4652, mailed Aug. 23, 2006 (corresponding to U.S. Appl. No. 11/443,274).

European Search Report for EP 06 11 4656, mailed Sep. 22, 2006 (corresponding to the present application).

European Search Report for EP 06 11 4655, mailed Sep. 22, 2006 (corresponding to U.S. Appl. No. 11/442,967).

French Report for FR 05 51445, mailed Feb. 6, 2006 (corresponding to U.S. Appl. No. 11/443,273).

French Report for FR 05 51444, mailed Feb. 6, 2006 (corresponding to U.S. Appl. No. 11/443,274).

French Report for FR 05 51429, mailed Feb. 1, 2006 (corresponding to the present application).

French Report for FR 05 51446, mailed Feb. 1, 2006 (corresponding to U.S. Appl. No. 11/442,967).

Boros et al., *J. Het. Chem.*, 38(3): 613-616 (2001).

Cohen & Zand, *J. Am. Chem. Soc.*, 84: 586-590 (1962).

Fonnum et al., *Colloid Polym. Sci*, 271(4): 380-389 (1993).

Heyman & Snyder, *Tetrahedron. Letters*, 30: 2859-2862 (1973).

Kharasch & Bruice, *J. Am. Chem. Soc.*, 73: 3240-3244 (1951).

Lingens and Shneider-Bernlöhr, *Justus Liebig Ann. Chem.*, 686: 134-144 (1965).

Magnien & Baltzly, *J. Org. Chem.*, 23: 2029-2032 (1958).

Stenzl et al., *Helvetica Chimia Acta*, 33: 1183-1194 (1950).

\* cited by examiner

COMPOSITION FOR DYEING KERATIN FIBERS, COMPRISING AT LEAST ONE DIAMINO-N,N-DIHYDROPYRAZOLONE DERIVATIVE, AT LEAST ONE COUPLER AND AT LEAST ONE ASSOCIATIVE POLYURETHANE POLYMER

This application claims benefit of U.S. Provisional Application No. 60/689,061, filed Jun. 10, 2005, the contents of which are incorporated herein by reference. This application also claims benefit of priority under 35 U.S.C. § 119 to French Patent Application No. FR 05 51429, filed May 31, 2005, the contents of which are also incorporated herein by reference.

The present disclosure relates to a composition for dyeing keratin fibers, for example, human keratin fibers such as the hair, comprising at least one oxidation base chosen from diamino-N,N-dihydropyrazolone compounds and addition salts thereof, at least one coupler and at least one associative polyurethane polymer, and also to the dyeing process using such a composition.

It is known practice to dye keratin fibers, for example human keratin fibers such as the hair, with dye compositions comprising oxidation dye precursors (also known as oxidation bases), e.g., ortho- or para-phenylenediamines, ortho- or para-aminophenols, and heterocyclic compounds such as diaminopyrazole derivatives, pyrazolo[1,5-a]pyrimidine derivatives, pyrimidine derivatives, pyridine derivatives, indole derivatives and indoline derivatives. Oxidation dye precursors, or oxidation bases, are colorless or weakly colored compounds that, when combined with oxidizing products, can give rise to colored compounds and dyes via a process of oxidative condensation. Permanent colorations are thus obtained.

It is also known that the shades obtained with these oxidation bases may be varied by combining them with couplers or coloration modifiers, the latter being chosen, for example, from meta-phenylenediamines, meta-aminophenols, meta-hydroxyphenols and certain heterocyclic compounds.

The variety of molecules used as regards the oxidation bases and couplers allows a wide range of colors to be obtained.

The use of oxidation bases such as para-phenylenediamine and para-aminophenol derivatives allows a quite broad range of colors to be obtained at basic pH but may not always result in shades with good chromaticity; at the same time the use of these bases may give the hair excellent properties in terms of strength of color, variety of shades, uniformity of the color and/or fastness with respect to external agents.

The use of these bases at neutral pH typically does not allow a varied range of shades to be produced, in particular for warm shades such as reds and oranges.

Thus, it would be desirable to provide novel compositions for dyeing keratin fibers that make it possible to obtain a strong, chromatic, aesthetic and/or sparingly selective coloration in varied shades, which shows good resistance to at least one of the various attacking factors to which the hair may be subjected, such as shampoo, light, sweat and permanent reshaping operations.

The present disclosure thus relates to a composition for dyeing keratin fibers, comprising, in a suitable medium:
at least one oxidation base chosen from diamino-N,N-dihydropyrazolone compounds of formula (I), and addition salts thereof:

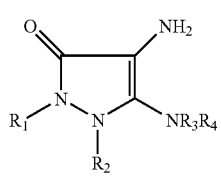

in which:
$R_1$, $R_2$, $R_3$ and $R_4$, which may be identical or different, are chosen from:
linear and branched $C_1$-$C_{10}$, such as $C_1$-$C_6$, alkyl radicals optionally substituted with at least one radical chosen from $OR_5$, $NR_6R_7$, carboxyl, sulfonic, carboxamido $CONR_6R_7$, and sulfonamido $SO_2NR_6R_7$ radicals and from heteroaryl or aryl radicals optionally substituted with at least one group chosen from $(C_1$-$C_4)$alkyl, hydroxyl, $C_1$-$C_2$ alkoxy, amino and $(di)(C_1$-$C_2)$alkylamino groups;
aryl radicals optionally substituted with at least one radical chosen from $(C_1$-$C_4)$alkyl, hydroxyl, $C_1$-$C_2$ alkoxy, amino and $(di)(C_1$-$C_2)$alkylamino radicals;
5- or 6-membered heteroaryl radicals, optionally substituted with at least one radical chosen from $(C_1$-$C_4)$alkyl and $(C_1$-$C_2)$alkoxy radicals;
$R_3$ and $R_4$ may also each independently be a hydrogen atom;
$R_5$, $R_6$ and $R_7$, which may be identical or different, are chosen from:
hydrogen atoms;
linear and branched $C_1$-$C_4$ alkyl radicals optionally substituted with at least one radical chosen from hydroxyl, $C_1$-$C_2$ alkoxy, carboxamido $CONR_8R_9$, sulfonyl $SO_2R_8$ and aryl radicals optionally substituted with at least one radical chosen from $(C_1$-$C_4)$alkyl, hydroxyl, $C_1$-$C_2$ alkoxy, amino and $(di)(C_1$-$C_2)$alkylamino radicals; aryl radicals optionally substituted with at least one radical chosen from $(C_1$-$C_4)$alkyl, hydroxyl, $C_1$-$C_2$ alkoxy, amino and $(di)(C_1$-$C_2)$alkylamino radicals;
$R_6$ and $R_7$, which may be identical or different, may also be chosen from carboxamido radicals $CONR_8R_9$; and sulfonyl radicals $SO_2R_8$;
$R_8$ and $R_9$, which may be identical or different, are chosen from hydrogen atoms; and from linear or branched $C_1$-$C_4$ alkyl radicals optionally substituted with at least one radical chosen from hydroxyl radicals and $C_1$-$C_2$ alkoxy radicals;
$R_1$ and $R_2$, on the one hand, and $R_3$ and $R_4$, on the other hand, may form, with the nitrogen atom(s) to which they are attached, saturated or unsaturated 5- to 7-membered heterocycles optionally substituted with at least one entity chosen from halogen atoms and from amino, $(di)(C_1$-$C_4)$alkylamino, hydroxyl, carboxyl, carboxamido and $(C_1$-$C_2)$alkoxy radicals, and $C_1$-$C_4$ alkyl radicals optionally substituted with at least one radical chosen form hydroxyl, amino, (di)alkylamino, alkoxy, carboxyl and sulfonyl radicals;
$R_3$ and $R_4$ may also form, together with the nitrogen atom to which they are attached, a 5- or 7-membered heterocycle, the carbon atoms of which may be replaced with an oxygen or optionally substituted nitrogen atom;
at least one coupler; and
at least one associative polyurethane polymer.

The present disclosure makes it possible to obtain a strong, aesthetic, and/or sparingly selective coloration of keratin fibers in varied shades, which shows good resistance to at least one of the various attacking factors to which the hair may be subjected, such as shampoo, light, sweat and permanent reshaping operations. It furthermore makes it possible to obtain intense and/or varied colorations at neutral pH.

Another subject of the present disclosure is a process for dyeing keratin fibers using the composition disclosed herein, and also the use of this composition for dyeing keratin fibers.

Finally, the present disclosure relates to a dyeing kit comprising, on the one hand, a dye composition comprising at least one oxidation base of formula (I), at least one coupler, and at least one associative polyurethane polymer and, on the other hand, a composition comprising at least one oxidizing agent.

In the context of the present disclosure, the term "alkyl radical" means linear or branched alkyl radicals which are $C_1$-$C_{10}$ unless otherwise indicated, for example $C_1$-$C_6$ and further for example $C_1$-$C_4$, such as methyl, ethyl, propyl, isopropyl, isobutyl, tert-butyl, pentyl and hexyl.

In at least one embodiment, in formula (I), the radicals $R_1$ and $R_2$, which may be identical or different, are chosen from:
  $C_1$-$C_6$ alkyl radicals optionally substituted with at least one radical chosen from hydroxyl, ($C_1$-$C_2$)alkoxy, amino and (di)($C_1$-$C_2$)alkylamino radicals;
  phenyl, methoxyphenyl, ethoxyphenyl and benzyl radicals.

In at least one embodiment, the radicals $R_1$ and $R_2$, which may be identical or different, are chosen from methyl, ethyl, 2-hydroxyethyl, 3-hydroxypropyl, 2-hydroxypropyl and phenyl radicals.

According to another embodiment, the radicals $R_1$ and $R_2$ form, together with the nitrogen atoms to which they are attached, a saturated or unsaturated, optionally substituted 5- or 6-membered ring. For example, the radicals $R_1$ and $R_2$ may form, together with the nitrogen atoms to which they are attached, a pyrazolidine or pyridazolidine ring, optionally substituted with at least one radical chosen from $C_1$-$C_4$ alkyl, hydroxyl, ($C_1$-$C_2$)alkoxy, carboxyl, carboxamido, amino and (di)($C_1$-$C_2$)alkylamino radicals.

In one embodiment, the radicals $R_1$ and $R_2$ form, together with the nitrogen atoms to which they are attached, a pyrazolidine or pyridazolidine ring.

As regards the radicals $R_3$ and $R_4$, which may be identical or different, they may be, in at least one embodiment, chosen from hydrogen atoms; linear or branched $C_1$-$C_6$ alkyl radicals optionally substituted with at least one radical chosen from hydroxyl, ($C_1$-$C_2$)alkoxy, amino and (di)($C_1$-$C_2$)alkylamino radicals; phenyl radicals optionally substituted with at least one radical chosen from hydroxyl, amino and ($C_1$-$C_2$)alkoxy radicals.

In one embodiment, the radicals $R_3$ and $R_4$, which may be identical or different, are chosen from hydrogen atoms and from methyl, ethyl, isopropyl, 2-hydroxyethyl, 3-hydroxypropyl, 2-hydroxypropyl and 2-carboxyethyl radicals. According to one embodiment, the radicals $R_3$ and $R_4$ are both a hydrogen atom.

According to another embodiment, the radicals $R_3$ and $R_4$ form, together with the nitrogen atom to which they are attached, a 5- or 7-membered ring chosen from pyrrolidine, piperidine, homopiperidine, piperazine and homopiperazine heterocycles; the rings possibly being substituted with at least one radical chosen from hydroxyl, amino, (di)($C_1$-$C_2$)alkylamino, carboxyl, carboxamido and $C_1$-$C_4$ alkyl radicals optionally substituted with at least one radical chosen from hydroxyl, amino and $C_1$-$C_2$ (di)alkylamino radicals.

For example, the radicals $R_3$ and $R_4$ may form, together with the nitrogen atom to which they are attached, a 5- or 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine and N-(2-hydroxyethyl)homopiperazine.

In at least one embodiment, the radicals $R_3$ and $R_4$ can form, together with the nitrogen atom to which they are attached, a 5- or 7-membered ring chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, hydroxypiperidine, homopiperidine, diazepane, N-methylhomopiperazine and N-β-hydroxyethylhomopiperazine.

In accordance with another embodiment, the radicals $R_3$ and $R_4$ form, together with the nitrogen atom to which they are attached, a 5-membered ring such as pyrrolidine, 3-hydroxypyrrolidine, 3-aminopyrrolidine or 3-dimethylaminopyrrolidine.

The compounds of formula (I) may be optionally salified with strong mineral acids, for instance HCl, HBr, Hl, $H_2SO_4$ or $H_3PO_4$, or organic acids, for instance acetic acid, lactic acid, tartaric acid, citric acid or succinic acid, benzenesulfonic acid, para-toluenesulfonic acid, formic acid or methanesulfonic acid.

They may also be in the form of solvates, for example a hydrate or a solvate of a linear or branched alcohol such as ethanol or isopropanol.

Non-limiting examples of derivatives of formula (I) that may be mentioned include the compounds presented below, or the addition salts thereof:
4,5-diamino-1,2-dimethyl-1,2-dihydropyrazol-3-one;
4-amino-5-methylamino-1,2-dimethyl-1,2-dihydropyrazol-3-one;
4-amino-5-dimethylamino-1,2-dimethyl-1,2-dihydropyrazol-3-one;
4-amino-5-(2-hydroxyethyl)amino-1,2-dimethyl-1,2-dihydropyrazol-3-one;
4-amino-5-(pyrrolidin-1-yl)-1,2-dimethyl-1,2-dihydropyrazol-3-one;
4-amino-5-(piperid-1-yl)-1,2-dimethyl-1,2-dihydropyrazol-3-one;
4,5-diamino-1,2-di(2-hydroxyethyl)-1,2-dihydropyrazol-3-one;
4-amino-5-methylamino-1,2-di(2-hydroxyethyl)-1,2-dihydropyrazol-3-one;
4-amino-5-dimethylamino-1,2-di(2-hydroxyethyl)-1,2-dihydropyrazol-3-one;
4-amino-5-(2-hydroxyethyl)amino-1,2-di(2-hydroxyethyl)-1,2-dihydropyrazol-3-one;
4-amino-5-(pyrrolidin-1-yl)-1,2-di(2-hydroxyethyl)-1,2-dihydropyrazol-3-one;
4-amino-5-(piperid-1-yl)-1,2-di(2-hydroxyethyl)-1,2-dihydropyrazol-3-one;
4,5-diamino-1,2-diethyl-1,2-dihydropyrazol-3-one;
4,5-diamino-1,2-phenyl-1,2-dihydropyrazol-3-one;

4,5-diamino-1-ethyl-2-methyl-1,2-dihydropyrazol-3-one;
4,5-diamino-2-ethyl-1-methyl-1,2-dihydropyrazol-3-one;
4,5-diamino-1-phenyl-2-methyl-1,2-dihydropyrazol-3-one;
4,5-diamino-2-phenyl-1-methyl-1,2-dihydropyrazol-3-one;
4,5-diamino-1-(2-hydroxyethyl)-2-methyl-1,2-dihydropyrazol-3-one;
4,5-diamino-2-(2-hydroxyethyl)-1-methyl-1,2-dihydropyrazol-3-one;
2,3-diamino-6,7-dihydro-1H,5H-pyrazolo[1,2-a]pyrazol-1-one;
2-amino-3-methylamino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(2-hydroxyethyl)amino-6,7-dihydro-1H,5H-pyrazolo[1,2-a]pyrazol-1-one;
2-amino-3-(2-hydroxypropyl)amino-6,7-dihydro-1H,5H-pyrazolo[1,2-a]pyrazol-1-one;
2-amino-3-bis(2-hydroxyethyl)amino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
2-amino-3-(3-hydroxypyrrolidin-1-yl)-6,7-dihydro-1H,5H-pyrazolo[1,2-a]pyrazol-1-one;
2-amino-3-(piperid-1-yl)-6,7-dihydro-1H,5H-pyrazolo[1,2-a]pyrazol-1-one;
2,3-diamino-6-hydroxy-6,7-dihydro-1H,5H-pyrazolo[1,2-a]pyrazol-1-one;
2,3-diamino-6-methyl-6,7-dihydro-1H,5H-pyrazolo[1,2-a]pyrazol-1-one;
2,3-diamino-6-dimethyl-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
2,3-diamino-5,8-dihydro-1H,6H-pyridazino[1,2-a]pyrazol-1-one;
4-amino-5-dimethylamino-1,2-diethyl-1,2-dihydropyrazol-3-one;
4-amino-1,2-diethyl-5-ethylamino-1,2-dihydropyrazol-3-one;
4-amino-1,2-diethyl-5-isopropylamino-1,2-dihydropyrazol-3-one;
4-amino-1,2-diethyl-5-(2-hydroxyethylamino)-1,2-dihydropyrazol-3-one;
4-amino-5-(2-dimethylaminoethylamino)-1,2-diethyl-1,2-dihydropyrazol-3-one;
4-amino-5-[bis(2-hydroxyethyl)amino]-1,2-diethyl-1,2-dihydropyrazol-3-one;
4-amino-1,2-diethyl-5-(3-imidazol-1-ylpropylamino)-1,2-dihydropyrazol-3-one;
4-amino-5-dimethylamino-1,2-diethyl-1,2-dihydropyrazol-3-one;
4-amino-1,2-diethyl-5-ethylamino-1,2-dihydropyrazol-3-one;
4-amino-1,2-diethyl-5-isopropylamino-1,2-dihydropyrazol-3-one;
4-amino-1,2-diethyl-5-(2-hydroxyethylamino)-1,2-dihydropyrazol-3-one;
4-amino-5-(2-dimethylaminoethylamino)-1,2-diethyl-1,2-dihydropyrazol-3-one;
4-amino-5-[bis(2-hydroxyethyl)amino]-1,2-diethyl-1,2-dihydropyrazol-3-one;

4-amino-1,2-diethyl-5-(3-imidazol-1-ylpropylamino)-1,2-dihydropyrazol-3-one;
4-amino-1,2-diethyl-5-(3-hydroxypyrrolidin-1-yl)-1,2-dihydropyrazol-3-one;
4-amino-1,2-diethyl-5-pyrrolidin-1-yl-1,2-dihydropyrazol-3-one;
4-amino-5-(3-dimethylaminopyrrolidin-1-yl)-1,2-diethyl-1,2-dihydropyrazol-3-one;
4-amino-1,2-diethyl-5-(4-methylpiperazin-1-yl)pyrazolidin-3-one;
2,3-diamino-6-hydroxy-6,7-dihydro-5H-pyrazolo[1,2-a]pyrazol-1-one;

some of which are given below to illustrate the names with chemical structures:

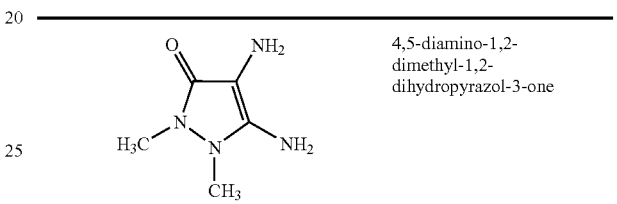

4,5-diamino-1,2-dimethyl-1,2-dihydropyrazol-3-one

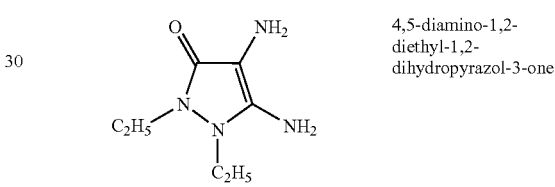

4,5-diamino-1,2-diethyl-1,2-dihydropyrazol-3-one

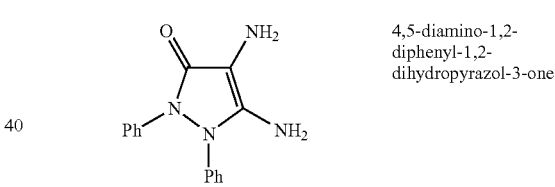

4,5-diamino-1,2-diphenyl-1,2-dihydropyrazol-3-one

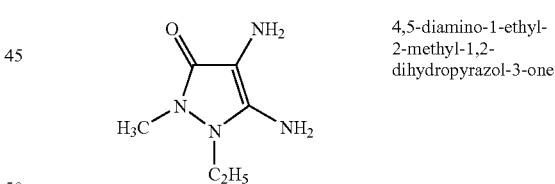

4,5-diamino-1-ethyl-2-methyl-1,2-dihydropyrazol-3-one

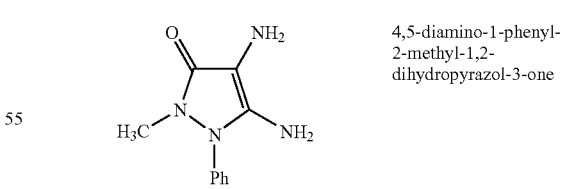

4,5-diamino-1-phenyl-2-methyl-1,2-dihydropyrazol-3-one

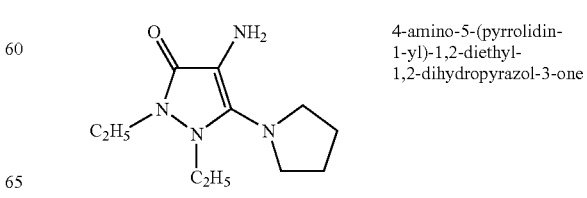

4-amino-5-(pyrrolidin-1-yl)-1,2-diethyl-1,2-dihydropyrazol-3-one

-continued

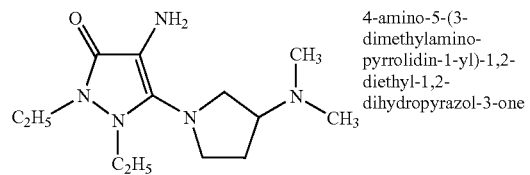
4-amino-5-(3-dimethylamino-pyrrolidin-1-yl)-1,2-diethyl-1,2-dihydropyrazol-3-one

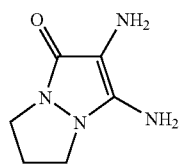
2,3-diamino-6,7-dihydro-1H,5H-pyrazolo[1,2-a]pyrazol-1-one

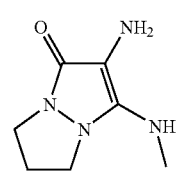
2-amino-3-methyl-amino-6,7-dihydro-1H,5H-pyrazolo[1,2-a]pyrazol-1-one

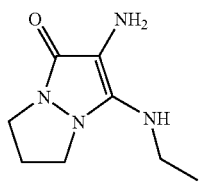
2-amino-3-ethylamino-6,7-dihydro-1H,5H-pyrazolo[1,2-a]pyrazol-1-one

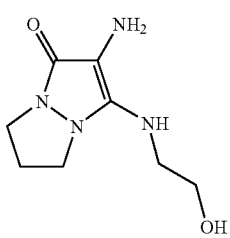
2-amino-3-(2-hydroxyethyl)amino-6,7-dihydro-1H,5H-pyrazolo[1,2-a]pyrazol-1-one

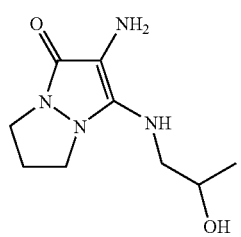
2-amino-3-(2-hydroxy-propyl)amino-6,7-dihydro-1H,5H-pyrazolo[1,2-a]pyrazol-1-one

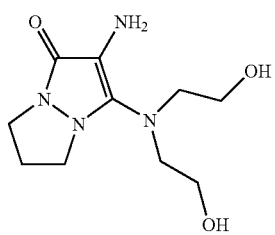
2-amino-3-bis(2-hydroxyethyl)amino-6,7-dihydro-1H,5H-pyrazolo[1,2-a]pyrazol-1-one

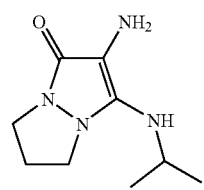
2-amino-3-iso-propylamino-6,7-dihydro-1H,5H-pyrazolo[1,2-a]pyrazol-1-one -continued

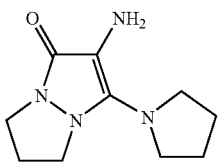
2-amino-3-(pyrrolidin-1-yl)-6,7-dihydro-1H,5H-pyrazolo[1,2-a]pyrazol-1-one

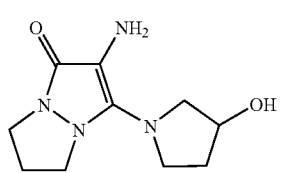
2-amino-3-(3-hydroxy-pyrrolidin-1-yl)-6,7-dihydro-1H,5H-pyrazolo[1,2-a]pyrazol-1-one

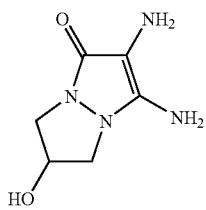
2,3-diamino-6-hydroxy-6,7-dihydro-1H,5H-pyrazolo[1,2-a]pyrazol-1-one

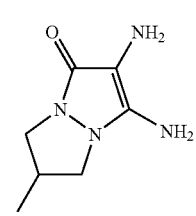
2,3-diamino-6-methyl-6,7-dihydro-1H,5H-pyrazolo[1,2-a]pyrazol-1-one

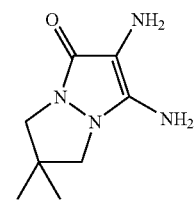
2,3-diamino-6,6-dimethyl-6,7-dihydro-1H,5H-pyrazolo[1,2-a]pyrazol-1-one

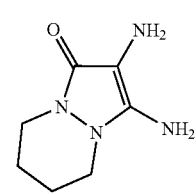
2,3-diamino-5,6,7,8-tetrahydro-1H,6H-pyridazino[1,2-a]pyrazol-1-one

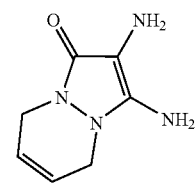
2,3-diamino-5,8-dihydro-1H,6H-pyridazino[1,2-a]pyrazol-1-one

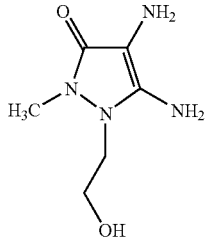
4,5-diamino-1-(2-hydroxyethyl)-2-methyl-1,2-dihydropyrazol-3-one

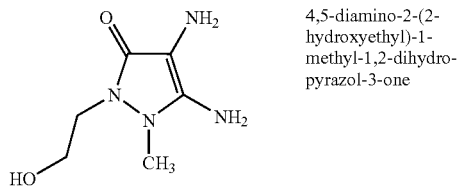

4,5-diamino-2-(2-hydroxyethyl)-1-methyl-1,2-dihydro-pyrazol-3-one

In at least one embodiment, the diamino-N,N-dihydropyrazolone compounds of formula (I), or the addition salts thereof, which may be useful herein include the following:

2,3-diamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
4,5-diamino-1,2-dimethyl-1,2-dihydropyrazol-3-one;
4,5-diamino-1,2-diethyl-1,2-dihydropyrazol-3-one;
4,5-diamino-1,2-di(2-hydroxyethyl)-1,2-dihydropyrazol-3-one;
2-amino-3-(2-hydroxyethyl)amino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
4-amino-1,2-diethyl-5-pyrrolidin-1-yl-1,2-dihydropyrazol-3-one;
4-amino-5-(3-dimethylaminopyrrolidin-1-yl)-1,2-diethyl-1,2-dihydropyrazol-3-one; and
2,3-diamino-6-hydroxy-6,7-dihydro-1H,5H-pyrazolo[1,2-a]pyrazol-1-one.

The at least one oxidation base of formula (I) is present (for each base) in an amount ranging from 0.001% to 10% by weight, such as from 0.005% to 6% by weight, relative to the total weight of the dye composition.

The at least one coupler useful herein may be chosen from meta-phenylenediamines, meta-aminophenols, meta-diphenols, naphthalene-based couplers, heterocyclic couplers, and the addition salts thereof.

Examples that may be mentioned, in a non-limiting manner, include 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene and 2,6-bis(β-hydroxyethylamino)toluene, and the acid-addition salts thereof.

In the composition of the present disclosure, the at least one coupler is present (for each coupler) in an amount ranging from 0.001% to 10% by weight, such as from 0.005% to 6% by weight, relative to the total weight of the dye composition.

The at least one associative polymer disclosed herein is, in at least one embodiment, chosen from water-soluble polymers whose molecules are capable, in aqueous medium, of reversibly associating with each other or with other molecules to lead to increased thickening of the medium.

The at least one associative polyurethane polymer that may be used in the context of the present disclosure comprises at least one end or side fatty chain having at least ten carbon atoms. These polymers are capable of interacting with themselves or with particular compounds of the medium in which they are present, such as surfactants, to lead to thickening of the medium. The associative polyurethane polymers may be cationic, anionic or nonionic.

Associative cationic polyurethane polymers that may be used include the compounds whose family has been described in French Patent No. 2,811,993; such as those of formula (II) below:

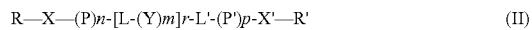

$$R—X—(P)n-[L-(Y)m]r-L'-(P')p-X'—R'$$ (II)

in which:

R and R', which may be identical or different, are chosen from hydrophobic groups and hydrogen atoms;

X and X', which may be identical or different, are chosen from groups comprising an amine functional group optionally bearing a hydrophobic group, or alternatively the group L";

L, L' and L", which may be identical or different, are each a group derived from a diisocyanate;

P and P', which may be identical or different, are each a group comprising an amine functional group optionally bearing a hydrophobic group;

Y is a hydrophilic group;

r is an integer ranging from 1 to 100, for example from 1 to 50, such as from 1 to 25;

n, m and p each range, independently of each other, from 0 to 1000;

wherein the molecule comprises at least one quaternary amine (protonated amine) or quaternized amine functional group and at least one hydrophobic group.

In one embodiment of these polyurethanes, the only hydrophobic groups are the groups R and R' at the chain ends.

In at least one embodiment, the family of cationic associative polyurethanes used is the one corresponding to formula (II) described above and in which:

R and R' are both independently a hydrophobic group, X and X' are each a group L", n and p range from 1 to 1,000, and L, L', L", P, P', Y and m have the meaning given above.

In another embodiment, the family of cationic associative polyurethanes used is the one corresponding to formula (II) above in which:

R and R' are both independently a hydrophobic group, X and X' are each a group L", n and p are 0, and L, L', L", Y and m have the meaning given above.

When n and p are 0, it means that these polymers do not comprise units derived from a monomer containing an amine functional group, incorporated into the polymer during the polycondensation. The protonated amine functional groups of these polyurethanes result from the hydrolysis of excess isocyanate functional groups, at the chain end, followed by alkylation of the primary amine functional groups formed with alkylating agents containing a hydrophobic group, i.e. compounds of the type RQ or R'Q, in which R and R' are as defined above and Q is a leaving group such as a halide, a sulfate, etc.

In yet another embodiment, the family of cationic associative polyurethanes used is the one corresponding to formula (II) above in which:

R and R' are both independently a hydrophobic group, X and X' are both independently a group comprising a quaternary amine, n and p are zero, and L, L', Y and m have the meaning given above.

The number-average molecular mass of the cationic associative polyurethanes ranges from 400 to 500,000, such as from 1,000 to 400,000, or from 1,000 to 300,000.

The expression "hydrophobic group" as used herein means a radical or polymer comprising a saturated or unsaturated, linear or branched hydrocarbon-based chain, which may comprise at least one heteroatom such as P, O, N or S, or a radical comprising a perfluoro or silicone chain. When the hydrophobic group is a hydrocarbon-based radical, it comprises at least 10 carbon atoms, for example from 10 to 30 carbon atoms, such as from 12 to 30 carbon atoms or from 18 to 30 carbon atoms.

In at least one embodiment, the hydrocarbon-based group is derived from a monofunctional compound.

By way of example, the hydrophobic group may be derived from a fatty alcohol such as stearyl alcohol, dodecyl alcohol or decyl alcohol. It may also be a hydrocarbon-based polymer such as, for example, polybutadiene.

When X and/or X' is a group comprising a tertiary or quaternary amine, X and/or X' may be chosen from one of the following formulae:

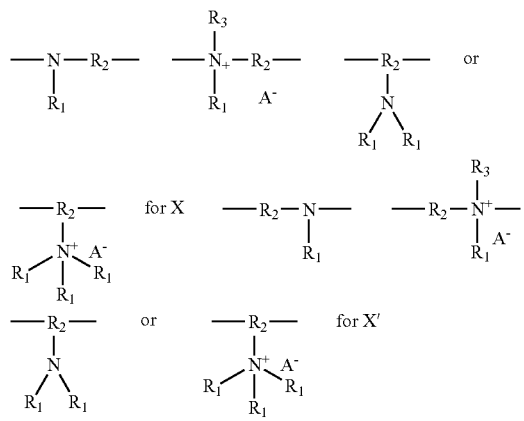

in which:

$R_2$ is chosen from linear and branched alkylene radicals comprising from 1 to 20 carbon atoms, optionally comprising a saturated or unsaturated ring, and from arylene radicals, wherein at least one of the carbon atoms is possibly replaced with a heteroatom chosen from N, S, O and P;

$R_1$ and $R_3$, which may be identical or different, are chosen from linear and branched $C_1$-$C_{30}$ alkyl radicals, linear and branched $C_1$-$C_{30}$ alkenyl radicals, and aryl radicals, which may comprise 1, 2 or 3 heteroatoms chosen from N, S, O and P; $A^-$ is a physiologically acceptable counterion.

The groups L, L' and L" are chosen from groups of formula:

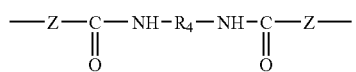

in which:

Z is chosen from —O—, —S— and —NH—; and $R_4$ is chosen from linear or branched alkylene radicals comprising from 1 to 20 carbon atoms, optionally comprising a saturated or unsaturated ring, and from arylene radicals, which may comprise 1, 2 or 3 heteroatoms chosen from N, S, O and P.

The groups P and P' comprising an amine functional group may be chosen from at least one of the following formulae:

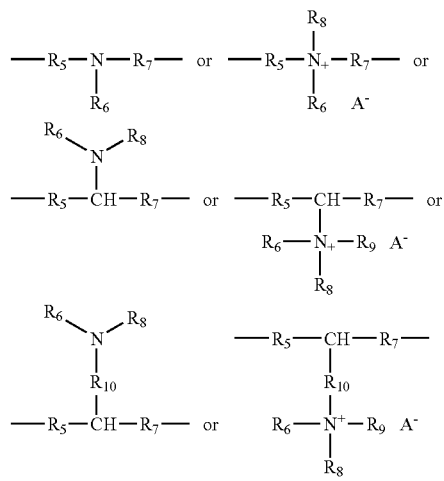

in which:

$R_5$ and $R_7$ have the same meanings as $R_2$ defined above;

$R_6$, $R_8$ and $R_9$ have the same meanings as $R_1$ and $R_3$ defined above; $R_{10}$ is a linear or branched, optionally unsaturated alkylene group, having, for example, 1-30 carbon atoms, such as 1-20 carbon atoms, or 1-10 carbon atoms, wherein said group may comprise 1, 2 or 3 heteroatoms chosen from N, O, S and P; and $A^-$ is a physiologically acceptable counterion.

As regards the meaning of Y as used herein, the term "hydrophilic group" means a polymeric or non-polymeric water-soluble group.

By way of example, when the hydrophilic group is not a polymer, it may be chosen from ethylene glycol, diethylene glycol and propylene glycol.

When it is a hydrophilic polymer, in accordance with one embodiment, the hydrophilic group may be chosen from polyethers, sulfonated polyesters, sulfonated polyamides and mixtures of these polymers. The hydrophilic compound is, in at least one embodiment, a polyether, such as a poly(ethylene oxide) or poly(propylene oxide).

The cationic associative polyurethanes of formula (II) that may be used according to the present disclosure are formed from diisocyanates and from various compounds with functional groups containing a labile hydrogen. The functional groups containing a labile hydrogen may be chosen from alcohol, primary or secondary amine and thiol functional groups, giving, after reaction with the diisocyanate functions, polyurethanes, polyureas and polythioureas, respectively. The expression "polyurethanes," as used according to the present disclosure, encompasses these three types of polymers, namely polyurethanes per se, polyureas and polythioureas, and also copolymers thereof.

A first type of compound involved in the preparation of the polyurethane of formula (II) is a compound comprising at least one unit containing an amine functional group. This compound may be multifunctional, but in at least one embodiment, the compound is difunctional, that is to say that, according to one embodiment, this compound comprises two labile hydrogen atoms borne, for example, by a hydroxyl, primary amine, secondary amine or thiol functional group. A mixture of multifunctional and difunctional compounds in which the percentage of multifunctional compounds is low may also be used.

As mentioned above, this compound may comprise more than one unit containing an amine functional group. In this case, it is a polymer bearing a repetition of the unit containing an amine functional group.

Compounds of this type may be represented by one of the following formulae:

$$HZ\text{-}(P)_n\text{-}ZH$$

or $$HZ\text{-}(P')_p\text{-}ZH$$

in which Z, P, P', n and p are as defined above.

Non-limiting examples of compounds containing an amine functional group that may be mentioned include N-methyldiethanolamine, N-tert-butyldiethanolamine and N-sulfoethyldiethanolamine.

The second compound involved in the preparation of the polyurethane of formula (II) is a diisocyanate corresponding to the formula:

$$O=C=N-R_4-N=C=O$$

in which $R_4$ is as defined above.

By way of example, non-limiting mention may be made of methylenediphenyl diisocyanate, methylenecyclohexane diisocyanate, isophorone diisocyanate, toluene diisocyanate, naphthalene diisocyanate, butane diisocyanate and hexane diisocyanate.

A third compound involved in the preparation of the polyurethane of formula (II) is a hydrophobic compound intended to form the terminal hydrophobic groups of the polymer of formula (II).

This compound comprises a hydrophobic group and a functional group comprising a labile hydrogen, said functional group being chosen, for example, from hydroxyl, primary or secondary amines, and thiol functional groups.

By way of non-limiting example, this compound may be a fatty alcohol such as stearyl alcohol, dodecyl alcohol or decyl alcohol. When this compound comprises a polymeric chain, it may be, for example, α-hydroxylated hydrogenated polybutadiene.

The hydrophobic group of the polyurethane of formula (II) may also result from the quaternization reaction of the tertiary amine of the compound comprising at least one tertiary amine unit. Thus, the hydrophobic group is introduced via the quaternizing agent. This quaternizing agent is a compound of the type RQ or R'Q, in which R and R' are as defined above and Q is a leaving group such as a halide or a sulfate.

The cationic associative polyurethane may also comprise a hydrophilic block. This block is provided by a fourth type of compound involved in the preparation of the polymer. This compound may be multifunctional, but in at least one embodiment it is difunctional. It is also possible to have a mixture in which the percentage of multifunctional compound is low.

The functional groups containing a labile hydrogen are chosen from alcohol, primary or secondary amine and thiol functional groups. This compound may be a polymer terminated at the chain ends with one of these functional groups containing a labile hydrogen.

By way of example, when the fourth type of compound is not a polymer, it may be chosen from, for example, ethylene glycol, diethylene glycol and propylene glycol.

When Y is a hydrophilic polymer, it may be chosen from, for example, polyethers, sulfonated polyesters and sulfonated polyamides, and from mixtures of these polymers. The hydrophilic compound, in at least one embodiment, is a polyether such as a poly(ethylene oxide) or poly(propylene oxide).

The hydrophilic group termed Y in formula (II) is optional. Specifically, the units containing a quaternary amine or protonated functional group may suffice to provide the solubility or water-dispersibility required for this type of polymer in an aqueous solution.

Although the presence of a hydrophilic group Y is optional, cationic associative polyurethanes comprising such a group are used in at least one embodiment.

Cationic associative polyurethanes according to the present disclosure that may be mentioned include the polymer having the name Polyurethane 16 according to the International Cosmetic Ingredient Dictionary & Handbook and sold by the company Chimex under the name MEXOMERE PAR, obtained by the condensation of N,N-dimethylethanolamine 1,3-bis(isocyanatomethylcyclohexane) quaternized with N,N-dimethylethanolamine polyoxyethylene bromodecane with a molecular weight of 10,000.

An example of an anionic associative polyurethane that may be used in at least one embodiment is an acrylic terpolymer that is soluble or swellable in alkalis and comprises:

a) 20% to 70% by weight, such as 25% to 55% by weight, of a carboxylic acid containing α,β-monoethylenic unsaturation;

b) 20% to 80% by weight, such as 30% to 65% by weight, of a non-surfactant monomer containing monoethylenic unsaturation, which is different from a), and c) 0.5% to 60% by weight, such as 10% to 50% by weight, of a nonionic urethane monomer which is the product of reaction of a monohydric nonionic surfactant with a monoisocyanate containing monoethylenic unsaturation.

The carboxylic acid containing α,β-monoethylenic unsaturation a) can be chosen from many acids, for example, it may be chosen from acrylic acid, methacrylic acid, itaconic acid and maleic acid. In at least one embodiment, methacrylic acid is used. A large proportion of acid is used in order to give a polymer structure which dissolves and gives a thickening effect by reaction with an alkaline compound such as sodium hydroxide, alkanolamines, aminomethylpropanol or aminomethylpropanediol.

The terpolymer may also contain a large proportion, indicated above, of a monomer b) containing monoethylenic unsaturation which has no surfactant properties. Monomers that may be used are those which give polymers that are water-insoluble when they are homopolymerized and are illustrated by $C_1$-$C_4$ alkyl acrylates and methacrylates such as methyl acrylate, ethyl acrylate and butyl acrylate, or corresponding methacrylates. For example, the monomers may be chosen from methyl and ethyl(meth)acrylates. Other monomers which can be used are styrene, vinyltoluene, vinyl acetate, acrylonitrile and vinylidene chloride. In at least one embodiment, non-reactive monomers are used, such monomers being those in which the single ethylenic group is the only group which is reactive under the polymerization conditions. However, monomers which contain groups that are reactive under the action of heat can be used in certain situations, such as hydroxyethyl acrylate.

The monohydric nonionic surfactants used to obtain the nonionic urethane monomer c) are well known and may be chosen from alkoxylated hydrophobic compounds containing an alkylene oxide forming the hydrophilic part of the molecule. The hydrophobic compounds comprise an aliphatic alcohol or an alkylphenol in which a carbon chain containing at least six carbon atoms constitutes the hydrophobic part of the surfactant.

The monohydric nonionic surfactants used in at least one embodiment have the formula:

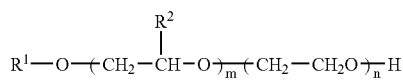

in which $R^1$ is chosen from $C_6$-$C_{30}$ alkyl and $C_8$-$C_{30}$ aralkyl groups, $R^2$ is a $C_1$-$C_4$ alkyl group, n is an average number ranging from 5 to 150 and m is an average number ranging from 0 to 50, with the condition that n is at least as large as m and that the sum n+m is from 5 to 150.

$C_6$-$C_{30}$ alkyl groups useful herein include dodecyl and $C_{18}$-$C_{26}$ alkyl radicals. As aralkyl groups, mention may be made, for example, of ($C_8$-$C_{13}$)alkylphenyl groups. In at least one embodiment, $R^2$ is methyl.

The monoisocyanate containing monoethylenic unsaturation which is used to form the nonionic urethane monomer c) can be chosen from a wide variety of compounds. A compound comprising any copolymerizable unsaturation such as acrylic or methacrylic unsaturation can be used. An allylic unsaturation imparted by allyl alcohol can also be used. In at least one embodiment, the monoethylenic monoisocyanates that may be used include α,α-dimethyl-m-isopropenyl-benzylisocyanate and methylstyrene-isopropylisocyanate. The acrylic terpolymer defined above is obtained by aqueous emulsion copolymerization of the components a), b) and c) which is known and described in European Patent Application EP-A-0 173 109.

As examples of anionic associative polyurethanes that may be used according to the present disclosure, mention may be made of copolymers of methacrylic or acrylic acid comprising at least one $C_{1-30}$ alkyl(meth)acrylate unit and a urethane unit substituted with a fatty chain. Non-limiting mention may be made, for instance, of the methacrylic acid/methyl methacrylate/methylstyrene-isopropyl isocyanate/behenyl alcohol polyethoxylated copolymer (comprising 40 ethoxy units) sold under the brand name Viscophobe® DB 1000 by the company Union Carbide.

The nonionic associative polyurethanes used in the present disclosure may, in at least one embodiment, be polyurethane polyethers comprising in their chain both hydrophilic blocks of polyoxyethylenated nature and hydrophobic blocks that may be aliphatic sequences alone and/or cycloaliphatic and/or aromatic sequences.

In at least one embodiment, the polyurethane polyethers comprise at least two hydrocarbon-based lipophilic chains comprising from 6 to 30 carbon atoms, separated by a hydrophilic block, the hydrocarbon-based chains possibly being pendent chains, or chains at the end of the hydrophilic block. For example, it is possible for at least one pendent chain to be included. In addition, the polymer may comprise a hydrocarbon-based chain at one end or at both ends of a hydrophilic block.

The polyurethane polyethers may be multiblock, such as in triblock form. Hydrophobic blocks may be at each end of the chain (for example: triblock copolymer with a hydrophilic central block) or distributed both at the ends and in the chain (for example: multiblock copolymer). These same polymers may also be graft polymers or starburst polymers.

The nonionic fatty-chain polyurethane polyethers may be triblock copolymers in which the hydrophilic block is a polyoxyethoxylated chain comprising from 50 to 1,000 ethoxylated groups. The nonionic polyurethane polyethers comprise a urethane linkage between the hydrophilic blocks, whence arises the name.

By extension, also included among the nonionic fatty-chain polyurethane polyethers are those in which the hydrophilic blocks are linked to the lipophilic blocks via other chemical bonds.

As examples of nonionic fatty-chain polyurethane polyethers that may be used herein, it is also possible to mention RHEOLATE 205 containing a urea functional group, sold by the company Rheox, or RHEOLATE 208, 204 or 212, and also Acrysol® RM 184. Mention may also be made of the product Elfacos® T210 containing a $C_{12-14}$ alkyl chain, and the product Elfacos® T212 containing a $C_{18}$ alkyl chain, from Akzo.

The product DW 1206B from Röhm & Haas containing a $C_{20}$ alkyl chain and a urethane linkage, sold at a solids content of 20% in water, may also be used.

It is also possible to use solutions or dispersions of these polymers, such as in water or in aqueous-alcoholic medium. Examples of such polymers that may be mentioned are Rheolate® 255, Rheolate® 278 and Rheolate® 244 sold by the company Rheox. The products DW 1206F and DW 1206J sold by the company Röhm & Haas may also be used.

The polyurethane polyethers that may be used according to the present disclosure include, for example, those described in the article by G. Fonnum, J. Bakke and F k. Hansen—Colloid Polym. Sci 271, 380-389 (1993).

In at least one embodiment, examples of nonionic associative polyurethanes that may be mentioned include polyurethane polyethers that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

Such polyurethane polyethers are sold, for instance, by the company Röhm & Haas under the names Aculyn® 46 and Aculyn® 44. Aculyn® 46 is a polycondensate of polyethylene glycol containing 150 or 180 mol of ethylene oxide, of stearyl alcohol and of methylenebis(4-cyclohexylisocyanate) (SMDI), at 15% by weight in a matrix of maltodextrin (4%) and water (81%); Aculyn® 44 is a polycondensate of polyethylene glycol containing 150 or 180 mol of ethylene oxide, of decyl alcohol and of methylenebis(4-cyclohexylisocyanate) (SMDI), at 35% by weight in a mixture of propylene glycol (39%) and water (26%).

According to at least one embodiment of the present disclosure, the at least one associative polyurethane polymer is cationic or nonionic.

The at least one associative polyurethane polymer is present in the composition in accordance with the disclosure, in at least one embodiment, in an amount ranging from 0.01% to 10% by weight relative to the total weight of the dye composition, such as from 0.1% to 5% by weight.

The dye composition disclosed herein may contain at least one oxidation base other than those of formula (I) and conventionally used for the dyeing of keratin fibers.

The composition of the present disclosure may comprise, for example, at least one additional oxidation base chosen from para-phenylenediamines, bis(phenyl)alkylenediamines, para-aminophenols, bis-para-aminophenols, ortho-aminophenols, ortho-phenylenediamines and heterocyclic bases other than the compounds of formula (I) as defined above, and the addition salts thereof.

Among the para-phenylenediamines that may be mentioned, for example, are para-phenylenediamine, para-tolylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-β-hydroxyethyl-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N-ethyl-N-(β-hydroxyethyl)-para-phenylenediamine, N-(β,-dihydroxypropyl)-para-phenylenediamine, N-(4'-aminophenyl)-para-phenylenediamine, N-phenyl-para-phenylenediamine, 2-β-hydroxyethyloxy-para-phenylenediamine, 2-β-acetylaminoethyloxy-para-phenylenediamine, N-(β-methoxyethyl)-para-phenylenediamine, 4-aminophenylpyrrolidine, 2-thienyl-para-phenylenediamine, 2-β-hydroxyethylamino-5-aminotoluene and 3-hydroxy-1-(4'-aminophenyl)pyrrolidine, and the acid-addition salts thereof.

Among the para-phenylenediamines mentioned above para-phenylenediamine, para-tolylenediamine, 2-isopropyl-para-phenylenediamine, 2-β-hydroxyethyl-para-phenylenediamine, 2-β-hydroxyethyloxy-para-phenylenediamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine and 2-β-acetylaminoethyloxy-para-phenylenediamine, and the acid-addition salts thereof may be used.

Among the bis(phenyl)alkylenediamines that may be mentioned, for example, are N,N'-bis(β-hydroxyethyl)-N,N'-bis(4'-aminophenyl)-1,3-diaminopropanol, N,N'-bis(β-hydroxyethyl)-N,N'-bis(4'-aminophenyl)ethylenediamine, N,N'-bis(4-aminophenyl)tetramethylenediamine, N,N'-bis(β-hydroxyethyl)-N,N'-bis(4-aminophenyl)-tetramethylenediamine, N,N'-bis(4-methylaminophenyl)tetramethylenediamine, N,N'-bis(ethyl)-N,N'-bis(4'-amino-3'-methylphenyl)ethylenediamine and 1,8-bis(2,5-diaminophenoxy)-3,6-dioxaoctane, and the acid-addition salts thereof.

Among the para-aminophenols that may be mentioned, for example, are para-aminophenol, 4-amino-3-methylphenol, 4-amino-3-fluorophenol, 4-amino-3-hydroxymethylphenol, 4-amino-2-methylphenol, 4-amino-2-hydroxymethylphenol, 4-amino-2-methoxymethylphenol, 4-amino-2-aminomethylphenol, 4-amino-2-(□-hydroxyethylaminomethyl)phenol and 4-amino-2-fluorophenol, and the acid-addition salts thereof.

Among the ortho-aminophenols that may be mentioned, for example, are 2-aminophenol, 2-amino-5-methylphenol, 2-amino-6-methylphenol and 5-acetamido-2-aminophenol, and the acid-addition salts thereof.

Among the heterocyclic bases, mention may be made, for example, of pyridine derivatives, pyrimidine derivatives and pyrazole derivatives.

Among the pyridine derivatives which may be mentioned are the compounds described, for example, in patents GB 1 026 978 and GB 1 153 196, as well as 2,5-diaminopyridine, 2-(4-methoxyphenyl)amino-3-aminopyridine, 2,3-diamino-6-methoxypyridine, 2-(β-methoxyethyl)amino-3-amino-6-methoxypyridine and 3,4-diaminopyridine, and the acid-addition salts thereof.

Other pyridine oxidation bases that are useful in the present disclosure are the 3-aminopyrazolo[1,5-a]pyridine oxidation bases or the addition salts thereof described, for example, in patent application FR 2 801 308. By way of example, mention may be made of pyrazolo[1,5-a]pyrid-3-ylamine; 2-acetylaminopyrazolo[1,5-a]pyrid-3-ylamine; 2-morpholin-4-ylpyrazolo[1,5-a]pyrid-3-ylamine; 3-aminopyrazolo[1,5-a]pyridine-2-carboxylic acid, 2-methoxypyrazolo[1,5-a]pyrid-3-ylamine; (3-aminopyrazolo[1,5-a]pyrid-7-yl)methanol; 2-(3-aminopyrazolo[1,5-a]pyrid-5-yl)ethanol; 2,3-aminopyrazolo[1,5-a]pyrid-7-yl)ethanol; (3-aminopyrazolo[1,5-a]pyrid-2-yl)methanol; 3,6-diaminopyrazolo[1,5-a]pyridine; 3,4-diaminopyrazolo[1,5-a]pyridine; pyrazolo[1,5-a]pyridine-3,7-diamine; 7-morpholin-4-yl-pyrazolo[1,5-a]pyrid-3-ylamine; pyrazolo[1,5-a]pyridine-3,5-diamine; 5-morpholin-4-ylpyrazolo[1,5-a]pyrid-3-ylamine; 2-[(3-aminopyrazolo[1,5-a]pyrid-5-yl)(2-hydroxyethyl)amino]ethanol; 2-[(3-aminopyrazolo[1,5-a]pyrid-7-yl)(2-hydroxyethyl)amino]ethanol; 3-aminopyrazolo[1,5-a]pyrid-5-ol; 3-aminopyrazolo[1,5-a]pyrid-4-ol; 3-aminopyrazolo[1,5-a]pyrid-6-ol; 3-aminopyrazolo[1,5-a]pyrid-7-ol and also the addition salts thereof with an acid or with a base.

Among the pyrimidine derivatives which may be mentioned are the compounds described, for example, in German Patent DE 2 359 399, Japanese Patent Nos. JP 88-169 571 and JP 05 163 124; European Patent EP 0 770 375, or patent application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine and 2,5,6-triaminopyrimidine, and pyrazolopyrimidine derivatives such as those mentioned in patent application FR-A-2 750 048 and among which mention may be made of pyrazolo[1,5-a]-pyrimidine-3,7-diamine; 2,5-dimethylpyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxyethyl)amino]ethanol, 2-[(7-aminopyrazolo[1,5-a]pyrimidin-3-yl)(2-hydroxyethyl)amino]ethanol, 5,6-dimethylpyrazolo[1,5-a]pyrimidine-3,7-diamine, 2,6-dimethylpyrazolo[1,5-a]pyrimidine-3,7-diamine, 2,5,N7,N7-tetramethylpyrazolo[1,5-a]pyrimidine-3,7-diamine and 3-amino-5-methyl-7-imidazolylpropylaminopyrazolo[1,5-a]pyrimidine, and the acid-addition salts thereof and the tautomeric forms thereof, when a tautomeric equilibrium exists.

Among the pyrazole derivatives which may be mentioned are the compounds described in German Patent Nos. DE 3 843 892 and DE 4 133 957 and patent applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3- dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethylpyrazole, 3,4,5-triaminopyrazole, 1-methyl-3,4,5-triaminopyrazole, 3,5-diamino-1-methyl-4-methylaminopyrazole and 3,5-diamino-4-(β-hydroxyethyl) amino-1-methylpyrazole, and the acid-addition salts thereof.

The at least one oxidation bases present in the composition of the present disclosure is each present (for each base) in an amount ranging from 0.001% to 10% by weight relative to the total weight of the dye composition, such as from 0.005% to 6%.

The addition salts of the oxidation bases and of the couplers that may be used in the context of the present disclosure are chosen, for example, from the acid-addition salts, such as the hydrochlorides, hydrobromides, sulfates, citrates, succinates, tartrates, lactates, tosylates, benzenesulfonates, phosphates and acetates, and the base-addition salts, such as sodium hydroxide, potassium hydroxide, ammonia, amines or alkanolamines.

The dye composition in accordance with the present disclosure may also comprise at least one direct dye, which may be chosen from nitrobenzene dyes, azo direct dyes and methine direct dyes. These direct dyes may be of nonionic, anionic or cationic nature.

The medium that is suitable for dyeing, also known as the dye support, is a cosmetic medium that comprises water or a mixture of water and at least one organic solvent to dissolve the compounds which would not be sufficiently soluble in water. As organic solvents that may be used, non-limiting mention may be made, for example, of $C_1$-$C_4$ lower alkanols, such as ethanol and isopropanol; polyols and polyol ethers such as 2-butoxyethanol, propylene glycol, propylene glycol monomethyl ether, diethylene glycol monoethyl ether and monomethyl ether, as well as aromatic alcohols such as benzyl alcohol or phenoxyethanol, and mixtures thereof.

The at least one solvent is present in an amount (for each solvent) ranging from 1% to 40% by weight relative to the total weight of the dye composition, such as from 5% to 30% by weight.

The dye composition in accordance with the present disclosure may also comprise at least one of various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or mixtures thereof, inorganic or organic thickeners, such as anionic, cationic and nonionic associative thickeners other than the associative polymers of polyurethane type and the amphoteric associative polymeric thickeners, antioxidants, penetrants, sequestrants, fragrances, buffers, dispersants, conditioning agents, for instance silicones, which may be volatile or non-volatile, and modified or unmodified, film-forming agents, ceramides, preserving agents and opacifiers.

The at least one adjuvant above can be present in an amount for each adjuvant) ranging from 0.01% to 20% by weight relative to the weight of the dye composition.

Needless to say, a person skilled in the art will take care to select this or optional additional compounds such that the advantageous properties intrinsically associated with the oxidation dye composition in accordance with the present disclosure are not, or are not substantially, adversely affected by the addition(s) envisaged.

The pH of the dye composition in accordance with the present disclosure ranges from 3 to 12, such as from 5 to 11. It may be adjusted to the desired value using acidifying or basifying agents usually used in the dyeing of keratin fibers, or alternatively using standard buffer systems.

Among the acidifying agents which may be mentioned, for example, are inorganic or organic acids such as hydrochloric acid, orthophosphoric acid, sulfuric acid, carboxylic acids such as acetic acid, tartaric acid, citric acid and lactic acid, and sulfonic acids.

Among the basifying agents which may be mentioned, for example, are aqueous ammonia, alkaline carbonates, alkanolamines such as mono-, di- and triethanolamine and derivatives thereof, sodium hydroxide, potassium hydroxide and the compounds of formula (III) below:

(III)

in which W is a propylene residue which is unsubstituted or substituted with a hydroxyl group or a $C_1$-$C_4$ alkyl radical; $R_a$, $R_b$, $R_c$ and $R_d$, which may be identical or different, are chosen from hydrogen atoms, $C_1$-$C_4$ alkyl radicals, and $C_1$-$C_4$ hydroxyalkyl radicals.

The dye composition according to the present disclosure may be in various forms, such as in the form of liquids, creams or gels, or in any other form that is suitable for dyeing keratin fibers, such as human hair.

The process disclosed herein is a process in which the composition according to the present disclosure as described above is applied to the fibers, and the color is developed using an oxidizing agent. The color may be developed at acidic, neutral or alkaline pH and the oxidizing agent may be added to the composition just at the time of use, or it may be used starting with an oxidizing composition containing it, which is applied simultaneously or sequentially to the composition. In at least one embodiment, this coloration is developed at neutral pH.

According to one embodiment, the composition according to the present disclosure is mixed, for example, at the time of use, with a composition containing, in a medium that is suitable for dyeing, at least one oxidizing agent, this oxidizing agent being present in an amount that is sufficient to develop a coloration. The mixture obtained is then applied to the keratin fibers. After an action time of 3 to 50 minutes, for example 5 to 30 minutes, the keratin fibers are rinsed, washed with shampoo, rinsed again and then dried.

The oxidizing agents conventionally used for the oxidation dyeing of keratin fibers are, for example, hydrogen peroxide, urea peroxide, alkali metal bromates, persalts such as perborates and persulfates, peracids and oxidase enzymes, among which mention may be made of peroxidases, 2-electron oxidoreductases such as uricases, and 4-electron oxygenases, for instance laccases. In at least one embodiment, hydrogen peroxide is used.

The oxidizing composition may also contain various adjuvants conventionally used in compositions for dyeing the hair and as defined above.

The pH of the oxidizing composition containing the oxidizing agent is such that, after mixing with the dye composition, the pH of the resulting composition applied to the keratin fibers ranges, in at least one embodiment, from 3 to 12, such as from 5 to 11. It may be adjusted to the desired value by means of acidifying or basifying agents usually used in the dyeing of keratin fibers and as defined above.

The ready-to-use composition that is finally applied to the keratin fibers may be in various forms, such as in the form of liquids, creams or gels or any other form that is suitable for dyeing keratin fibers, such as human hair.

Another subject of the present disclosure is a multi-compartment dyeing device or "kit", in which at least one first compartment comprises the dye composition of the present disclosure as defined above with the exception of the oxidizing agent and at least one second compartment comprises an oxidizing composition comprising at least one oxidizing agent. This device may be equipped with a means for applying the desired mixture to the hair, such as the devices described in French Patent FR-2 586 913.

A subject of the present disclosure is also the use for the oxidation dyeing of keratin fibers, and that includes human keratin fibers such as the hair, of a composition as defined above.

The diamino-N,N-dihydropyrazolone derivatives of formula (I) may be obtained from synthetic intermediates and synthetic routes described in the literature and, for instance, in the following documents: J. Het. Chem., 2001, 38(3), 613-616, Helvetica Chimica Acta, 1950, 33, 1183-1194, J. Org. Chem., 23, 2029 (1958), J. Am. Chem. Soc., 73, 3240 (1951), J. Am. Chem. Soc., 84, 590 (1962), Justus Liebig Ann. Chem., 686, 134 (1965), Tetrahedron. Lett., 31, 2859-2862 (1973), and U.S. Pat. Nos. 4,128,425 and 2,841,584 and the documents cited therein.

According to these documents, the compounds of formula (I) in which the radicals $R_3$ and $R_4$ are equal to hydrogen atoms may be obtained via the synthetic route represented by scheme A below:

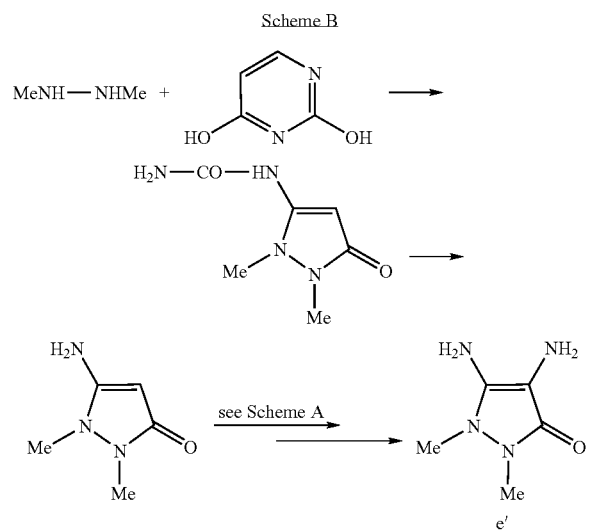

The compounds in which the radicals $R_1$ and $R_2$ are simultaneously methyl groups and the radicals $R_3$ and $R_4$ are both hydrogen atoms may be obtained on the basis of the method described in Justus Lieb. Ann. Chem., 686, 134 (1965) (Scheme B):

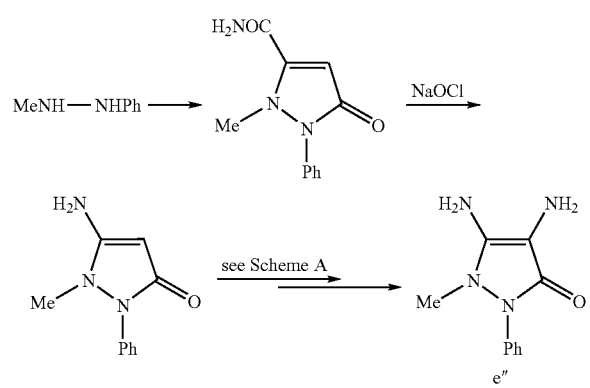

The compounds in which the radical $R_1$ is a methyl group, $R_2$ is a phenyl radical and the radicals $R_3$ and $R_4$ are both hydrogen atoms may be obtained on the basis of the method described in J. Org. Chem., 23, 2029 (1958), J. Am. Chem. Soc., 73, 3240 (1951) (Scheme C):

The compounds in which the radicals $R_1$ and $R_2$ together form a 5-membered ring and in which the radicals $R_3$ and $R_4$ are both hydrogen atoms may be obtained on the basis of the method described in J. Het. Chem., 2001, 38(3), 613-616 (Scheme D):

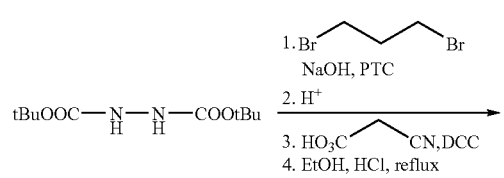

-continued

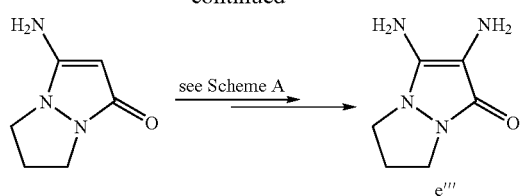

According to a different process, the compounds of formula (I) may be obtained according to the synthesis illustrated in Scheme E:

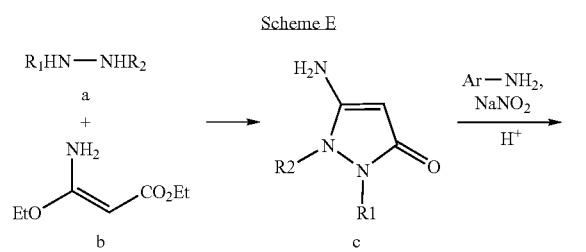

According to this process, the following steps are performed:

a) Step 1: a compound a

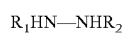

is reacted with a compound b:

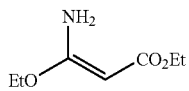

to obtain a 5-amino-1,2-dihydropyrazol-3-one compound c:

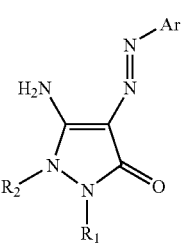

b) Step 2: the derivative c thus obtained is reacted with an aryldiazonium salt ($ArNH_2$, $NaNO_2$, $H^+$) to obtain an azo compound f:

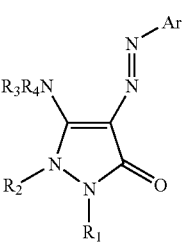

c) Step 3: a step of functionalization of the primary amine group of the resulting azo compound f is optionally performed to obtain a compound g below:

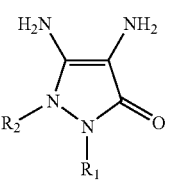

d) Step 4: a reduction reaction of the azo compound f or g is performed to obtain, respectively, an amino compound e or h:

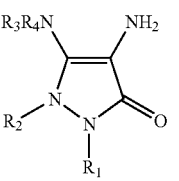

The optional step of functionalization of the primary amine group in position 5 to a secondary and tertiary amine $NR_3R_4$, to obtain the compounds g, is performed according to the standard methods of organic synthesis (alkyl halide, alkyl O-sulfonate, alkyl trialkylammonium, reductive amination, etc., see, for example, *Advanced Organic Chemistry*, 3rd edition, 1985, J. March, Wiley Interscience).

Reduction of the azo group leads to the compounds e and h in accordance with the present disclosure.

The reduction step is performed in a conventional manner, for example by performing a hydrogenation reaction via heterogeneous catalysis in the presence of Pd/C, Pd(II)/C, Ni/Ra, etc. or alternatively by performing a reduction reaction with a metal, for example with zinc, iron, tin, etc. (see Advanced Organic Chemistry, 3rd edition, J. March, 1985, Wiley Interscience and Reduction in Organic Chemistry, M. Hudlicky, 1983, Ellis Horwood Series Chemical Science).

According to another process, the 2,3-diamino-6,7-dihydro-1H,5H-pyrazolo[1,2-a]pyrazol-1-one and 2,3-diamino-5,6,7,8-tetrahydro-1H,6H-pyridazino[1,2-a]-pyrazol-1-one derivatives are obtained according to the synthesis illustrated by Scheme F:

is reacted with a compound a2:

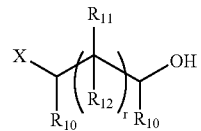

a2

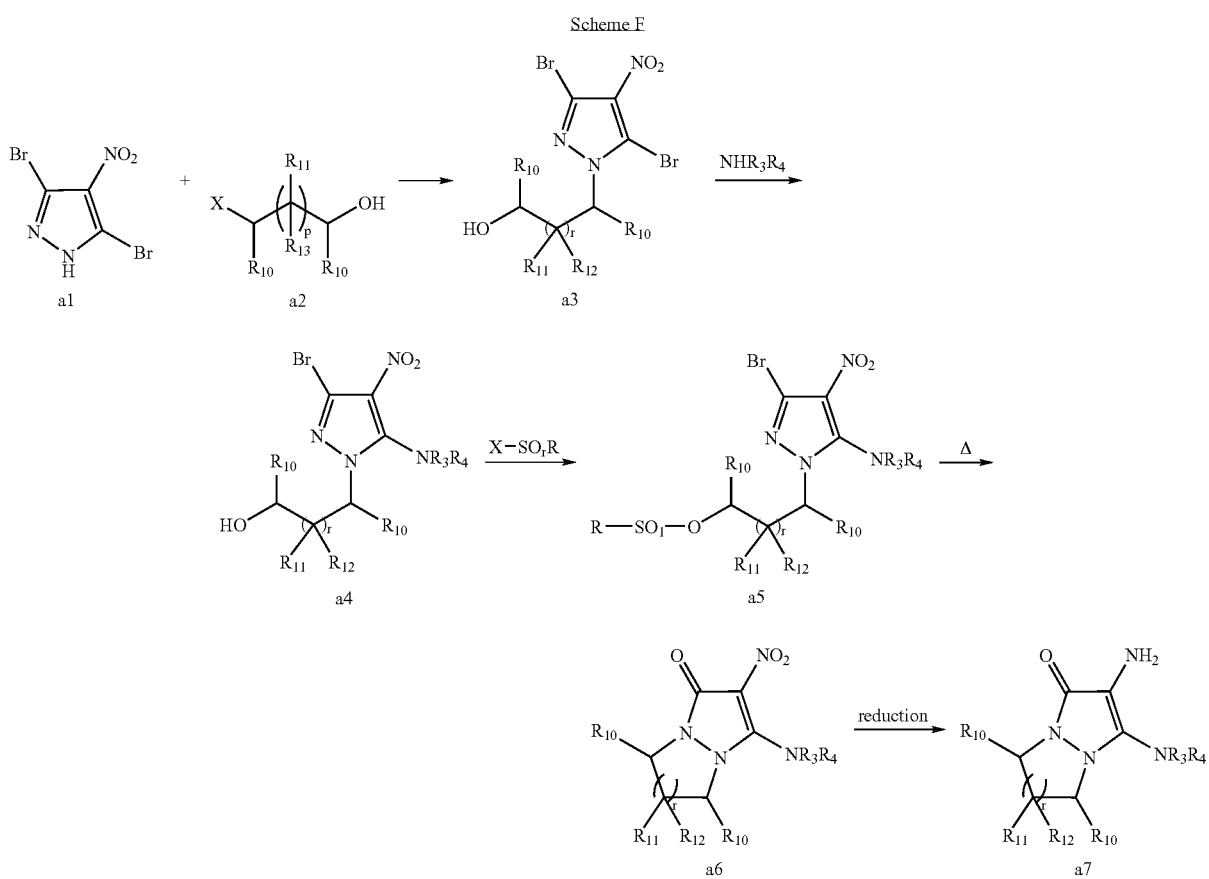

According to this process, the following steps are performed:

a) Step 1: a compound a1 below:

a1 is reacted with a compound a2 to obtain a compound a3:

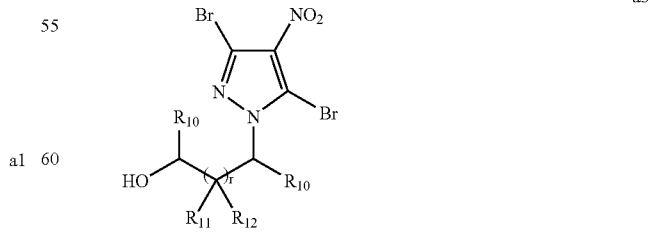

a3 in which:
the radical $R_{10}$ is a hydrogen atom, a carboxyl; a carboxamido; a $C_1$-$C_4$ alkyl radical optionally substituted with at least one radical chosen from hydroxyl, amino, (di)alkylamino, alkoxy, carboxyl and sulfonyl radicals;

the radicals $R_{11}$ and $R_{12}$ are, independently of each other, chosen from hydrogen atoms, halogen atoms; and amino; (di)($C_1$-$C_4$)alkylamino; hydroxyl; carboxyl; carboxamido; ($C_1$-$C_2$)alkoxy; and $C_1$-$C_4$ alkyl radicals optionally substituted with at least one radical chosen from hydroxyl, amino, (di)alkylamino, alkoxy, carboxyl and sulfonyl radicals;

X is chosen from a halogen atom and an alkylsulfonate;

r is an integer from 1 to 3.

b) Step 2: compound a3 is reacted with an amine of formula $NHR_3R_4$ to obtain a compound a4:

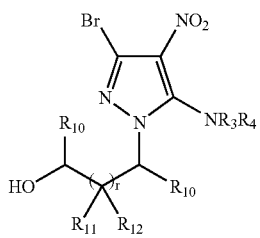

a4 c) Step 3: compound a4 is reacted with at least one alkylsulfonyl, arylsulfonyl or perfluoroalkylsulfonyl halide $R-O_2S-X_1$ (R is chosen from alkyl, aryl and perfluoroalkyl, $X_1$ is a halogen), in a solvent with a boiling point ranging from 60° C. to 190° C., to obtain a compound a5:

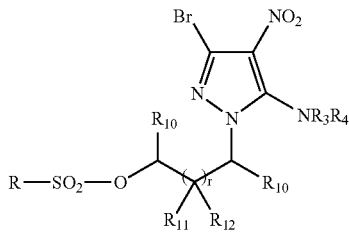

a5 d) Step 4: the resulting compound a5 is then heated in a solvent with a boiling point ranging from 60° C. to 190° C. to obtain a compound a6:

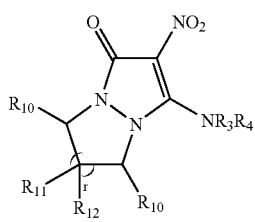

a6 e) Step 5: the compound a6 obtained is reduced to obtain the compound a7 of formula (IV) below:

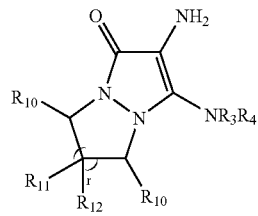

a7

Formula (IV)

In at least one embodiment, according to this process, the 3,5-dibromo-4-nitropyrazole a1, obtained, for example, according to the method described in German Patent DE 4 234 885, reacts with the reagent a2, for example in a solvent with a boiling point ranging from 60° C. to 190° C. Examples that may be mentioned include pentanol, dimethylformamide and N-methylpyrrolidine. In at least one embodiment, the reaction is performed in the presence of an organic or mineral base, for instance sodium carbonate, sodium hydroxide, sodium acetate or triethylamine. The temperature of the reaction medium is, in at least one embodiment, maintained at a range from 60° C. to 160° C. such as from 80° C. to 120° C.

In at least one embodiment, the 1-hydroxyalkyl-3,5-dibromo-4-nitropyrazole a3 is isolated by precipitation or crystallization after addition of ice to the reaction medium.

In step 2, the derivative a3 is reacted with an amine $NHR_3R_4$, for example in a solvent with a boiling point ranging from 60° C. to 190° C., for instance butanol, pentanol or dimethylformamide. In at least one embodiment, the temperature ranges from 60° C. to 160° C., such as from 80° C. to 120° C. After consumption of the reagents, the 5-amino-4-nitro-3-bromo-1-hydroxyalkylpyrazole compound a4 is isolated by precipitation or crystallization from water.

In accordance with step 3, the derivative a5 is obtained by reacting the alcohol a4 and an alkylsulfonyl, arylsulfonyl or perfluoroalkylsulfonyl halide. In at least one embodiment, the reaction takes place in an aprotic solvent, for instance tetrahydrofuran or dioxane. In at least one embodiment, the reaction takes place at a temperature of from −20° C. to 60° C., such as from 0° C. to 25° C. Furthermore, this step takes place in the presence of an organic or mineral base, for instance potassium carbonate, triethylamine or N-methylmorpholine. After disappearance of the reagents, compound a5 is isolated by precipitation or crystallization from water.

The sulfonate a5 obtained after step 3 is placed, in step 4, in solution or in dispersion in a solvent with a boiling point ranging from 60° C. to 190° C., such as from 90° C. to 140° C. The temperature of the reaction medium is then brought to 90° C. to 140° C., such as from 105° C. to 125° C. until all of the sulfonate a5 has been consumed. After cooling to room temperature, the perhydropyrazolo[1,2-a]pyrazol-1-one (r=1), perhydropyridazino[1,2-a]pyrazol-1-one (r=2) or perhydrodiazepino[1,2-a]pyrazolone (r=3) compound a6 crystallizes and is isolated via the standard methods of organic synthesis.

The final compound a7 in accordance with the present disclosure is obtained, during a step 5, via reduction of the nitro derivative a6, the reduction methods used being, for example, a hydrogenation via heterogeneous catalysis in the presence of Pd/C, Pd(II)/C, Ni/Ra, etc. or alternatively such as a reduction reaction with a metal, for example with zinc, iron, tin, etc. (see Advanced Organic Chemistry, 3rd edition, J. March, 1985, Wiley Interscience and Reduction in Organic Chemistry, M. Hudlicky, 1983, Ellis Horwood Series Chemical Science).

Other than in the examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific examples are reported as precisely as possible. Any numerical value, however, inherently contain certain errors necessarily resulting from the standard deviation found in their respective testing measurements.

The examples that follow serve to illustrate the present disclosure without, however, being limiting in nature.

EXAMPLES

Example 1

Synthesis of 2,3-diamino-6,7-dihydro-1H,5H-pyrazolo[1,2-a]pyrazol-1-one dihydrochloride 5

Step 1: Synthesis of 3-(3,5-dibromo-4-nitro-1H-pyrazol-1-yl)propan-1-ol 1

0.369 mol of sodium acetate was introduced into a solution of 0.184 mol of dibromonitropyrazole in 250 ml of N-methylpyrrolidone in a 500 ml three-necked flask, and the reaction medium was brought to 80° C.

0.369 mol of 3-bromopropanol was added dropwise at this temperature. This temperature was maintained for 5 hours.

After cooling to room temperature, the medium was poured onto ice with stirring.

The 3-(3,5-dibromo-4-nitro-1H-pyrazol-1-yl)propan-1-ol 1 precipitated. It was filtered off by suction, dried and obtained in a yield of 75%.

The mass of the expected compound $C_6H_7Br_2N_3O_3$ was detected by mass spectrometry.

The NMR analyses ($^1$H 400 MHz and $^{13}$C 100.61 MHz DMSO $d_6$) were in accordance with the expected structure.

Step 2: Synthesis of 3-[5-(benzylamino)-3-bromo-4-nitro-1H-pyrazol-1-yl]propan-1-ol 2

0.135 mol of 3-(3,5-dibromo-4-nitro-1H-pyrazol-1-yl)propan-1-ol 1 was dispersed in a 500 ml three-necked flask containing 150 ml of ethanol, the mixture was heated to 60° C. and 0.825 mol of benzylamine was then added over 30 minutes.

After 6 hours at 60° C., the reaction medium was cooled to room temperature.

The 3-[5-(benzylamino)-3-bromo-4-nitro-1H-pyrazol-1-yl]propan-1-ol 2 was precipitated by pouring the reaction medium onto 1 liter of ice with stirring. After filtration by suction and drying under vacuum in the presence of $P_2O_5$, compound 2 was isolated in a yield of 90%.

The NMR analyses ($^1$H 400 MHz and $^{13}$C 100.61 MHz DMSO $d_6$) were in accordance with the expected structure.

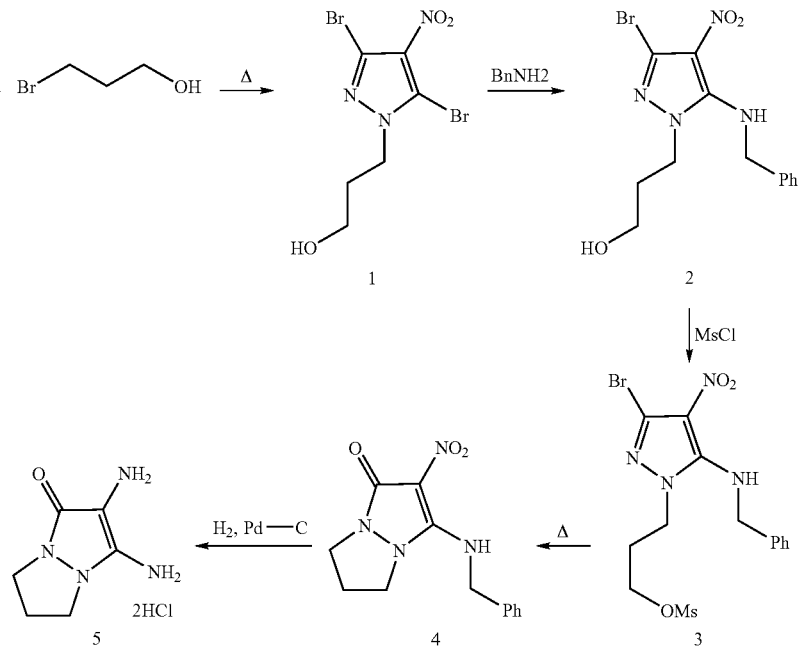

| Elemental analysis: | | | | |
|---|---|---|---|---|
| Theory: C43.96 | H4.26 | N15.77 | O13.51 | Br22.50 |
| Found: C44.09 | H4.22 | N15.44 | O14.37 | Br21.50 |

Step 3: Synthesis of 3-[5-(benzylamino)-3-bromo-4-nitro-1H-pyrazol-1-yl]propyl methanesulfonate 3

0.126 mol of 3-[5-(benzylamino)-3-bromo-4-nitro-1H-pyrazol-1-yl]propan-1-ol 2 and 15.82 mol of triethylamine were introduced, with stirring, into a 500 ml three-necked flask containing 200 ml of THF. The mixture obtained was then cooled to 5° C. and 0.126 mol of mesyl chloride was poured in over 45 minutes.

The reaction medium was maintained at this temperature for 2 hours and the 3-[5-(benzylamino)-3-bromo-4-nitro-1H-pyrazol-1-yl]propyl methanesulfonate 3 was then precipitated by pouring the reaction medium onto 800 ml of ice.

After filtering, the solid was washed thoroughly with water and with diisopropyl ether. Drying was performed under vacuum in the presence of $P_2O_5$. The yield for this step was 94%.

The mass of the expected compound $C_{14}H_{17}BrN_4O_5S$ was detected by mass spectrometry.

The NMR analyses ($^1$H 400 MHz and $^{13}$C 100.61 MHz DMSO $d_6$) were in accordance with the expected structure.

| Elemental analysis: | | | | | |
|---|---|---|---|---|---|
| Theory: C38.81 | H3.96 | N12.93 | O18.46 | S7.40 | Br18.44 |
| Found: C39.03 | H3.91 | N12.83 | O18.52 | S7.29 | Br18.26 |

Step 4: Synthesis of 3-(benzylamino)-2-nitro-6,7-dihydro-1H,5H-pyrazolo[1,2-a]pyrazol-1-one 4

0.1 mol of 3-[5-(benzylamino)-3-bromo-4-nitro-1H-pyrazol-1-yl]propyl methanesulfonate 3 was dispersed in a 500 ml three-necked flask containing 300 ml of pentanol, and the reaction medium was maintained at 130° C. for 2 hours.

After cooling to room temperature, the solid formed was filtered off by suction on a sinter funnel, washed with diisopropyl ether and dried under vacuum in the presence of $P_2O_5$. The 3-(benzylamino)-2-nitro-6,7-dihydro-1H,5H-pyrazolo[1,2-a]pyrazol-1-one 4 was obtained in a yield of 86%.

The NMR analyses ($^1$H 400 MHz and $^{13}$C 100.61 MHz DMSO $d_6$) were in accordance with the expected structure.

The mass of the expected compound $C_6H_{11}N_4O$ was detected by mass spectrometry.

| Elemental analysis: | | | |
|---|---|---|---|
| Theory: C56.72 | H5.49 | N20.36 | O17.44 |
| Found: C56.68 | H5.13 | N20.38 | O17.69 |

Step 5: Synthesis of 2,3-diamino-6,7-dihydro-1H,5H-pyrazolo[1,2-a]pyrazol-1-one dihydrochloride 5

20 g of 3-(benzylamino)-2-nitro-6,7-dihydro-1H,5H-pyrazolo[1,2-a]pyrazol-1-one 4 and 4 g of 5% palladium-on-charcoal were introduced into a 1 liter autoclave containing 800 ml of ethanol. The reduction was then performed under a hydrogen pressure of 8 bar and at a temperature of from 50° C. to 100° C. (stirring of from 1,000 to 2,500 rpm).

After reaction for 4 hours, there was no further consumption of hydrogen and the medium was cooled to 20° C.

The catalyst was removed under nitrogen by filtration, and hydrochloric ethanol was then added to the filtrate. The crystalline product was filtered off by suction, washed with diisopropyl ether and then dried under vacuum in the presence of $P_2O_5$. The 2,3-diamino-6,7-dihydro-1H,5H-pyrazolo[1,2-a]pyrazol-1-one dihydrochloride 5 was obtained in a yield of 89%.

The mass of the expected compound was detected by mass spectrometry.

The NMR analyses ($^1$H 400 MHz and $^{13}$C 100.61 MHz DMSO $d_6$) were in accordance with the expected structure.

| Elemental analysis: | | | | |
|---|---|---|---|---|
| Theory: C31.73 | H5.33 | N24.67 | O7.07 | Cl31.22 |
| Found: C31.45 | H5.20 | N24.62 | O7.24 | Cl30.86 |

Example 2

Synthesis of 2-amino-3-(ethylamino)-6,7-dihydro-1H,5H-pyrazolo[1,2-a]pyrazol-1-one dihydrochloride 9

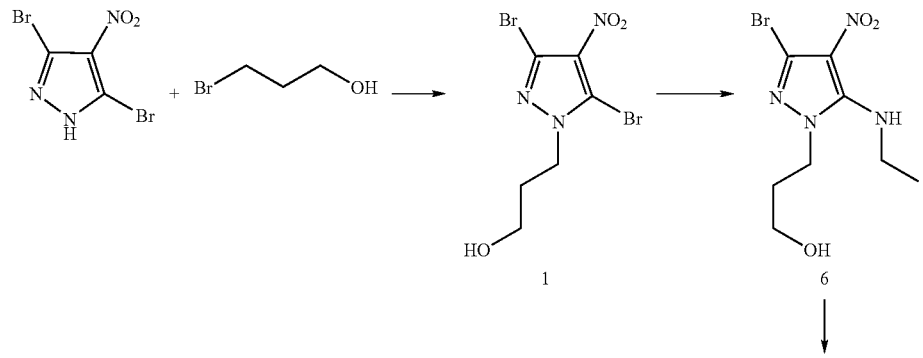

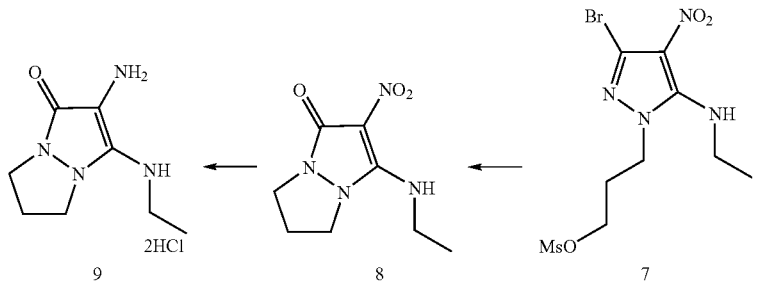

Step 2: Synthesis of 3-[3-bromo-5-(ethylamino)-4-nitro-1H-pyrazol-1-yl]propan-1-ol 6

15 mmol of 3-(3,5-dibromo-4-nitro-1H-pyrazol-1-yl)propan-1-ol were introduced into 30 ml of ethanol in a three-necked flask, with stirring. The homogeneous medium was heated to 75° C. and 93 mmol of ethylamine were then added dropwise and stirring was continued for four hours.

After cooling to room temperature, the medium was poured onto ice and the 3-[3-bromo-5-(ethylamino)-4-nitro-1H-pyrazol-1-yl]propan-1-ol 6 precipitated.

The yellow solid was filtered off by suction and then washed thoroughly with water and diisopropyl ether. Drying was performed under vacuum in the presence of $P_2O_5$. The recovered mass was 3.6 g.

The NMR analyses ($^1$H 400 MHz and $^{13}$C 100.61 MHz DMSO $d_6$) were in accordance with the expected structure.

The mass of the expected compound $C_8H_{13}BrN_4O_3$ was detected by mass spectrometry.

Step 3: Synthesis of 3-[5-(ethylamino)-3-bromo-4-nitro-1H-pyrazol-1-yl]propyl methanesulfonate 7

11.2 mmol of 3-[3-bromo-5-(ethylamino)-4-nitro-1H-pyrazol-1-yl]propan-1-ol 6 and 1.6 ml of triethylamine were introduced, with stirring, into a 100 ml three-necked flask containing 30 ml of THF. The homogeneous orange mixture obtained was cooled to 0° C. and 1.44 ml of mesyl chloride were added over 20 minutes.

The reaction medium was maintained at this temperature for 2 hours and the 3-[5-(ethylamino)-3-bromo-4-nitro-1H-pyrazol-1-yl]propyl methanesulfonate 7 was precipitated by pouring the reaction medium onto 500 ml of ice.

The yellow solid was filtered by suction and then washed thoroughly with water and diisopropyl ether; drying was performed under vacuum in the presence of $P_2O_5$. The recovered mass was 3.1 g.

The NMR analyses ($^1$H 400 MHz and $^{13}$C 100.61 MHz DMSO $d_6$) were in accordance with the expected structure.

The mass of the expected compound $C_9H_{15}BrN_4O_5S$ was detected by mass spectrometry.

Step 4: Synthesis of 3-(ethylamino)-2-nitro-6,7-dihydro-1H,5H-pyrazolo[1,2-a]pyrazol-1-one 8

8 mmol of 3-[5-(ethylamino)-3-bromo-4-nitro-1H-pyrazol-1-yl]propyl methanesulfonate 7 were dispersed, with stirring, in a 50 ml three-necked flask containing 20 ml of pentanol, and the reaction medium was maintained at 130° C. for 2 hours.

After cooling to room temperature, the solid formed was filtered off by suction and then washed with diisopropyl ether.

After drying under vacuum in the presence of $P_2O_5$, 1.46 g of 3-(ethylamino)-2-nitro-6,7-dihydro-1H,5H-pyrazolo[1,2-a]pyrazol-1-one 8 were obtained.

The NMR analyses ($^1$H 400 MHz and $^{13}$C 100.61 MHz DMSO $d_6$) were in accordance with the expected structure.

The mass of the expected compound was detected by mass spectrometry.

Step 5: Synthesis of 2-amino-3-(ethylamino)-6,7-dihydro-1H,5H-pyrazolo[1,2-a]pyrazol-1-one dihydrochloride 9

1.45 g of 3-(ethylamino)-2-nitro-6,7-dihydro-1H,5H-pyrazolo[1,2-a]pyrazol-1-one 8 and 300 mg of 5% palladium-on-charcoal were introduced into a 300 ml autoclave containing 200 ml of ethanol. The reduction was performed at a hydrogen pressure of 8 bar at a temperature of 60° C. (stirring at 1700 rpm).

After reaction for 2 hours, there was no further consumption of hydrogen and the reaction medium was cooled to 20° C.

The catalyst was removed by filtration under nitrogen and the filtrate was diluted with 100 ml of hydrochloric isopropyl ether.

The pale yellow solution was evaporated to dryness and the solid was then taken up in an ethanol/isopropyl ether mixture. The 2-amino-3-(ethylamino)-6,7-dihydro-1H,5H-pyrazolo[1,2-a]pyrazol-1-one hydrochloride 9 precipitated; it was filtered off by suction and, after drying under vacuum in the presence of $P_2O_5$, 1.18 g of 2-amino-3-(ethylamino)-6,7-dihydro-1H,5H-pyrazolo[1,2-a]pyrazol-1-one dihydrochloride 9 were recovered.

The NMR analyses ($^1$H 400 MHz and $^{13}$C 100.61 MHz DMSO $d_6$) were in accordance with the expected structure.

The mass of the expected compound $C_8H_{14}N_4O$ was detected by mass spectrometry.

Example 3

Synthesis of 2-amino-3-(isopropylamino)-6,7-dihydro-1H,5H-pyrazolo[1,2-a]pyrazol-1-one 13

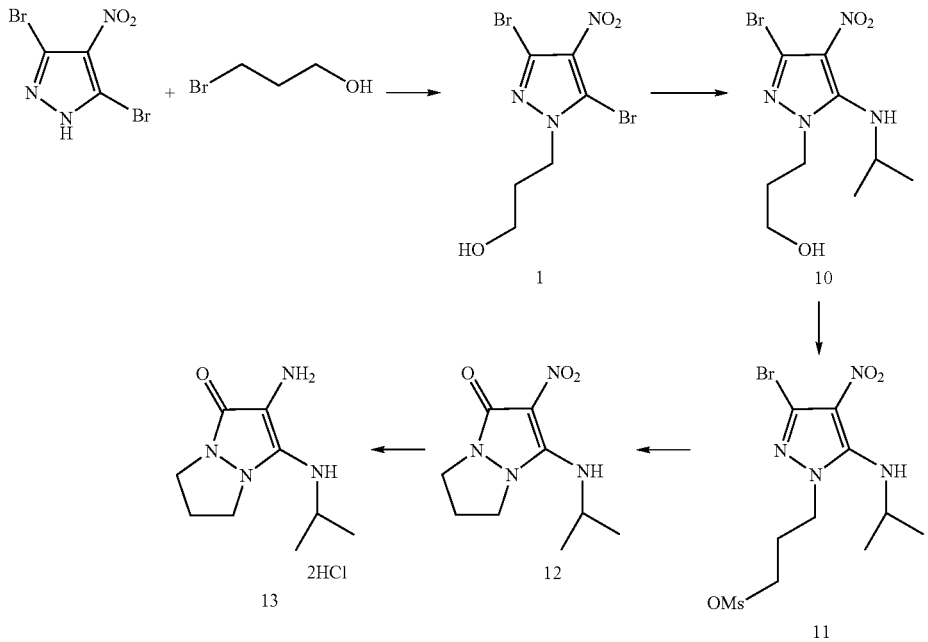

Step 2: Synthesis of 3-[3-bromo-5-(isopropylamino)-4-nitro-1H-pyrazol-1-yl]propan-1-ol 10

15 mmol of 3-(3,5-dibromo-4-nitro-1H-pyrazol-1-yl)propan-1-ol were introduced, with stirring, into 30 ml of ethanol in a three-necked flask. The homogeneous medium was heated to 75° C. and 93 mmol of isopropylamine were then added dropwise with continued stirring for 4 hours.

After cooling to room temperature, the medium was poured onto ice and then neutralized with hydrochloric acid. The 3-[3-bromo-5-(isopropylamino)-4-nitro-1H-pyrazol-1-yl]propan-1-ol 10 was extracted with dichloromethane.

After drying the organic phase over sodium sulfate and removing the solvent by evaporation under vacuum, 4.37 g of 3-[3-bromo-5-(isopropylamino)-4-nitro-1H-pyrazol-1-yl]propan-1-ol 10 were obtained.

The NMR analyses ($^1$H 400 MHz and $^{13}$C 100.61 MHz DMSO $d_6$) were in accordance with the expected structure.

The mass of the expected compound $C_9H_{15}BrN_4O_3$ was detected by mass spectrometry.

Step 3: Synthesis of 3-[5-(isopropylamino)-3-bromo-4-nitro-1H-pyrazol-1-yl]propyl methanesulfonate 11

13.7 mmol of 3-[3-bromo-5-(isopropylamino)-4-nitro-1H-pyrazol-1-yl]propan-1-ol 10 and 1.94 ml of triethylamine were introduced, with stirring, into a 50 ml three-necked flask containing 20 ml of THF. The homogeneous orange mixture thus obtained was cooled to 0° C. and 1.76 ml of mesyl chloride were added over 20 minutes.

The reaction medium was maintained at this temperature for 2 hours, and 3-[5-(ethylamino)-3-bromo-4-nitro-1H-pyrazol-1-yl]propyl methanesulfonate 11 was then precipitated by pouring the reaction medium onto 500 ml of ice.

The yellow solid was filtered off by suction and then washed thoroughly with water and petroleum ether, and was dried under vacuum in the presence of $P_2O_5$. The recovered mass was 4.2 g.

The NMR analyses ($^1$H 400 MHz and $^{13}$C 100.61 MHz DMSO $d_6$) were in accordance with the expected structure.

The mass of the expected compound was detected by mass spectrometry.

Step 4: Synthesis of 3-(isopropylamino)-2-nitro-6,7-dihydro-1H,5H-pyrazolo[1,2-a]pyrazol-1-one 12

10 mmol of 3-[5-(isopropylamino)-3-bromo-4-nitro-1H-pyrazol-1-yl]propyl methanesulfonate 11 are dispersed, with stirring, in 20 ml of pentanol in a 50 ml three-necked flask, and the mixture was heated at 130° C. for 2 hours.

After cooling to room temperature, the solid obtained was filtered off by suction on a sinter funnel and washed with diisopropyl ether.

After drying under vacuum in the presence of $P_2O_5$, 1.71 g of 3-(isopropylamino)-2-nitro-6,7-dihydro-1H,5H-pyrazolo[1,2-a]pyrazol-1-one 12 were obtained.

The NMR analyses ($^1$H 400 MHz and $^{13}$C 100.61 MHz DMSO $d_6$) were in accordance with the expected structure.

The mass of the expected compound $C_9H_{14}N_4O_3$ was detected by mass spectrometry.

Step 5: Synthesis of 2-amino-3-(isopropylamino)-6,7-dihydro-1H,5H-pyrazolo[1,2-a]pyrazol-1-one dihydrochloride 13

1.70 g of 3-(isopropylaminoamino)-2-nitro-6,7-dihydro-1H,5H-pyrazolo[1,2-a]pyrazol-1-one 12 and 300 mg of 5% palladium-on-charcoal were introduced into a 300 ml autoclave containing 200 ml of ethanol. The reaction was performed at a temperature of 60° C. and at a hydrogen pressure of 6 bar (stirring at 2,000 rpm).

After reaction for 2 hours, there was no further consumption of hydrogen, and the medium was cooled to 20° C.

The catalyst was removed by filtration under nitrogen after cooling to room temperature, and hydrochloric isopropyl ether was added.

The pale yellow solution was evaporated to dryness and the solid was then taken up in 50 ml of diisopropyl ether saturated with hydrogen chloride, and the precipitate was recovered by suction filtration. After drying under vacuum in the presence of $P_2O_5$, 1.5 g of 2-amino-3-(isopropylamino)-6,7-dihydro-1H,5H-pyrazolo[1,2-a]pyrazol-1-one dihydrochloride 13 were isolated.

The NMR analyses ($^1$H 400 MHz and $^{13}$C 100.61 MHz DMSO $d_6$) were in accordance with the expected structure.

The mass of the expected compound $C_9H_{16}N_4O$ was detected by mass spectrometry.

Example 4

2-Amino-3-(pyrrolidin-1-yl)-6,7-dihydro-1H,5H-pyrazolo[1,2-a]pyrazol-1-one dihydrochloride 17

After drying the organic phase over sodium sulfate and distilling off the solvent by evaporation under vacuum, 4.8 g of 3-(3-bromo-4-nitro-5-(pyrrolidin-1-yl)-1H-pyrazol-1-yl)propan-1-ol 14 were obtained.

The NMR analyses ($^1$H 400 MHz and $^{13}$C 100.61 MHz DMSO $d_6$) were in accordance with the expected structure.

The mass of the expected compound $C_{10}H_{17}BrN_4O$ was detected by mass spectrometry.

Step 3: Synthesis of 3-(3-bromo-4-nitro-5-(pyrrolidin-1-yl)-1H-pyrazol-1-yl)propyl methanesulfonate 15

30 mmol of 3-(3-bromo-4-nitro-5-(pyrrolidin-1-yl)-1H-pyrazol-1-yl)propan-1-ol 14 and 4.25 ml of triethylamine were introduced, with stirring, into a 100 ml three-necked flask containing 50 ml of THF. The homogeneous orange mixture obtained was cooled to 0° C. and 2.32 ml of mesyl chloride were added over 20 minutes.

The reaction medium was maintained at this temperature for 2 hours and the 3-(3-bromo-4-nitro-5-(pyrrolidin-1-yl)-1H-pyrazol-1-yl)propyl methanesulfonate 15 was then precipitated by pouring the reaction medium onto ice.

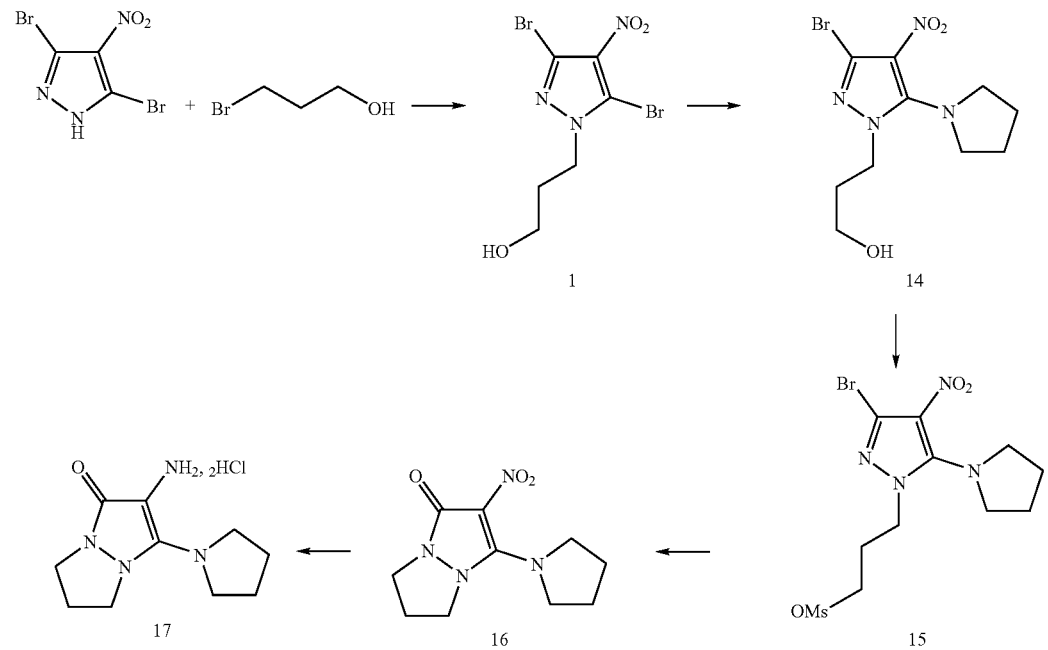

Step 2: 3-(3-Bromo-4-nitro-5-(pyrrolidin-1-yl)-1H-pyrazol-1-yl)propan-1-ol 14

15 mmol of 3-(3,5-dibromo-4-nitro-1H-pyrazol-1-yl)propan-1-ol were introduced, with stirring, into 20 ml of isopropanol in a three-necked flask. The homogeneous medium was heated to 75° C. and 90 mmol of pyrrolidine were then added dropwise and stirring was continued for 2 hours.

After cooling to room temperature, the medium was poured onto ice and neutralized with hydrochloric acid. The 3-(3-bromo-4-nitro-5-(pyrrolidin-1-yl)-1H-pyrazol-1-yl)propan-1-ol 14 was extracted with dichloromethane.

The solid was filtered off by suction and then dried under vacuum in the presence of $P_2O_5$. The recovered mass was 9.3 g.

The NMR analyses ($^1$H 400 MHz and $^{13}$C 100.61 MHz DMSO $d_6$) were in accordance with the expected structure.

The mass of the expected compound $C_{11}H_{19}BrN_4O_3S$ was detected by mass spectrometry.

Step 4: Synthesis of 2-nitro-3-(pyrrolidin-1-yl)-6,7-dihydro-1H,5H-pyrazolo[1,2-a]pyrazol-1-one 16

22.5 mmol of 3-(3-bromo-4-nitro-5-(pyrrolidin-1-yl)-1H-pyrazol-1-yl)propyl methanesulfonate 15 were introduced into 100 ml of pentanol, with stirring, in a 250 ml three-necked flask. The medium thus obtained was maintained at 130° C. for 2 hours.

After cooling to room temperature, the 2-nitro-3-(pyrrolidin-1-yl)-6,7-dihydro-1H,5H-pyrazolo[1,2-a]pyrazol-1-one 16 was extracted with dichloromethane.

After drying the organic phase over sodium sulfate and distilling off the solvent under vacuum, 1.2 g of 2-nitro-3-pyrrolidin-1-yl-6,7-dihydro-1H,5H-pyrazolo[1,2-a]pyrazol-1-one 16 were obtained.

The NMR analyses ($^1$H 400 MHz and $^{13}$C 100.61 MHz DMSO d$_6$) were in accordance with the expected structure.

The mass of the expected compound $C_{10}H_{14}N_4O_3$ was detected by mass spectrometry.

Step 5: Synthesis of 2-amino-3-(pyrrolidin-1-yl)-6,7-dihydro-1H,5H-pyrazolo[1,2-a]pyrazol-1-one dihydrochloride 17

1.1 g of 2-nitro-3-(pyrrolidin-1-yl)-6,7-dihydro-1H,5H-pyrazolo[1,2-a]pyrazol-1-one 16 and 300 mg of 5% palladium-on-charcoal were introduced into a 300 ml autoclave containing 200 ml of ethanol. The reduction was performed with stirring at 2,000 rpm, at a temperature of 60° C. and under a hydrogen pressure of 6 bar.

After reaction for 2 hours, there was no further consumption of hydrogen, and the medium was cooled to 20° C.

The catalyst was removed by filtration under nitrogen after cooling to room temperature, and hydrochloric isopropyl ether was added.

The pale yellow solution was evaporated to dryness and the solid was then taken up in 50 ml of diisopropyl ether saturated with hydrogen chloride, and the precipitate was recovered by suction filtration. After drying under vacuum in the presence of $P_2O_5$, 1.5 g of 2-amino-3-(pyrrolidin-1-yl)-6,7-dihydro-1H,5H-pyrazolo[1,2-a]pyrazol-1-one dihydrochloride 17 were obtained.

The NMR analyses ($^1$H 400 MHz and $^{13}$C 100.61 MHz DMSO d$_6$) were in accordance with the expected structure.

The mass of the expected compound $C_{10}H_{16}N_4O$ was detected by mass spectrometry.

Example 5

Synthesis of 2,3-diamino-6,7-dihydro-1H,5H-pyrazolo[1,2-a]pyrazol-1-one dimethanesulfonate

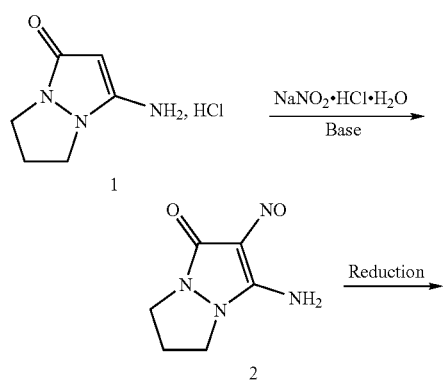

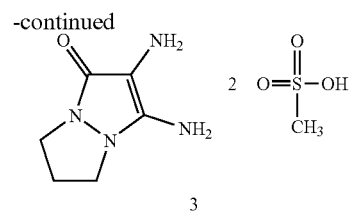

Synthesis of 3-amino-2-nitroso-6,7-dihydro-1H,5H-pyrazolo[1,2-a]pyrazol-1-one: 2

43 g (0.245 mol) of 3-amino-6,7-dihydro-1H,5H-pyrazolo[1,2-a]pyrazol-1-one hydrochloride were dissolved, with stirring, at room temperature, in a mixture of 180 ml of water and 35 ml of 35% hydrochloric acid in a 500 ml three-necked flask.

The mixture was cooled to 0° C. and a solution of 17.3 g of sodium nitrite (0.25 mol) in 20 ml of water was added dropwise over 30 minutes. The temperature of the reaction medium was maintained at a range of from 0 to +5° C. throughout the addition and for one hour after the end of the addition.

The reaction medium was brought to pH 8 by adding sodium hydroxide, with stirring, while maintaining the temperature at a range of from 0 to 5° C. The 3-amino-2-nitroso-6,7-dihydro-1H,5H-pyrazolo[1,2-a]pyrazol-1-one 2 precipitates in the form of a red-orange solid, which was filtered off on a No. 4 sinter funnel, slurried in a minimum amount of 2-propanol, washed with diisopropyl ether and dried under vacuum in the presence of phosphorus pentoxide. 35 g of orange-red product were thus obtained (yield: 85%).

The NMR ($^1$H 400 MHz and $^{13}$C 100.61 MHz DMSO d$_6$) and mass spectra were in accordance with the expected structure 2.

Synthesis of 2,3-diamino-6,7-dihydro-1H,5H-pyrazolo[1,2-a]pyrazol-1-one dimethanesulfonate: 3

33.6 g (0.2 mol) of 3-amino-2-nitroso-6,7-dihydro-1H,5H-pyrazolo[1,2-a]pyrazol-1-one 2, 500 ml of ethanol and 6 g of 5% palladium-on-charcoal containing 50% water were introduced into a 1 liter autoclave.

The medium was flushed 3 times with nitrogen and then 3 times with hydrogen and the temperature of the mixture was brought to 40° C.

The reduction was performed over two hours at a pressure of 8 bar. This reduction was exothermic and the temperature spontaneously rose to 70° C.

The temperature was allowed to fall to 50° C. and the catalyst was then filtered off on a filterpress under a stream of nitrogen.

The filtrate was poured into a mixture of 50 ml of ethanol and 40 ml of methanesulfonic acid, with cooling to 0° C. The 2,3-diamino-6,7-dihydro-1H,5H-pyrazolo-[1,2-a]pyrazol-1-one dimethanesulfonate 3 crystallized in the form of a pale yellow solid, which was filtered off by suction on a No. 4 sinter funnel, washed with diisopropyl ether and then with petroleum ether and finally dried under vacuum in the presence of phosphorus pentoxide. 43 g of pale yellow solid were thus obtained (yield: 65%).

The NMR ($^1$H 400 MHz and $^{13}$C 100.61 MHz DMSO d$_6$) and mass spectra were in accordance with the expected structure 3.

Elemental analysis:

| | | | | | |
|---|---|---|---|---|---|
| Theory: | C27.74 | H5.23 | N16.17 | O32.33 | S18.51 |
| Found: | C27.16 | H5.22 | N15.63 | O32.81 | S18.64 |

Example 6

Synthesis of 2,3-diamino-5,6,7,8-tetrahydro-1H-pyrazolo[1,2-a]pyridazin-1-one hydrochloride

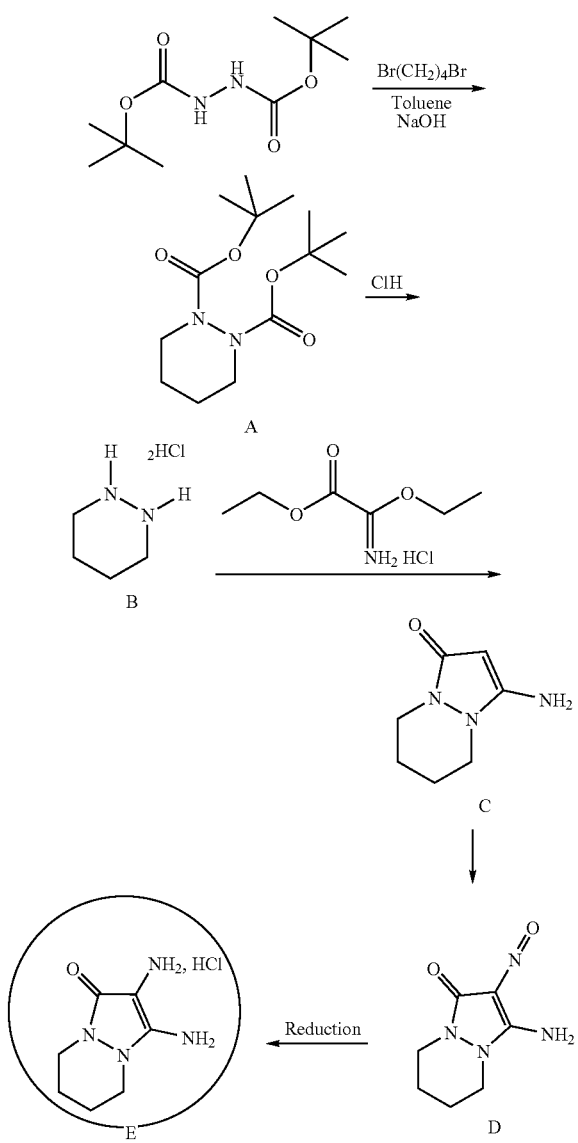

Synthesis of di-tert-butyl tetrahydropyridazine-1,2-dicarboxylate: A 50 ml of toluene, 5 g (21.5 mmol) of N,N'-di-tert-butoxycarbonyl hydrazide, 680 mg of tetraethylammonium bromide and 25 ml of 50% sodium hydroxide were introduced, with mechanical stirring, into a 250 ml three-necked flask equipped with a condenser, a thermometer and a dropping funnel.

The heterogeneous medium was heated to 100° C. and 1,4-dibromobutane was then added dropwise over 15 minutes.

The reaction medium was heated at 100° C. for 3 days. After cooling, 100 ml of ethyl acetate were added and the mixture was transferred into a separating funnel. The organic phase was washed with 4 times 70 ml of saturated aqueous sodium carbonate solution and then with 4×70 ml of water and finally with 4×70 ml of brine. The organic phase was dried over sodium sulfate and the solvent was evaporated off under vacuum. A colorless oil that crystallized as a white solid was thus obtained.

A mass of 6.1 g was recovered (yield: 99%).

The NMR ($^1$H 400 MHz and $^{13}$C 100.61 MHz DMSO $d_6$) and mass spectra were in accordance with the expected structure A.

Synthesis of Hexahydropyridazine Dihydrochloride: B 5.9 g of compound A were introduced into 50 ml of a 3/1 mixture of dioxane and 35% hydrochloric acid, with mechanical stirring, in a 100 ml three-necked flask equipped with a condenser and a thermometer.

The colorless solution obtained was stirred at room temperature for 3 hours and the reaction medium was then diluted with diisopropyl ether. The solvents were evaporated off under vacuum. The pasty residue obtained was taken up in an ether/ethanol mixture. After filtering off the solid and drying under vacuum, 1.39 g of white solid were obtained.

The NMR ($^1$H 400 MHz and $^{13}$C 100.61 MHz DMSO $d_6$) and mass spectra were in accordance with the expected structure B.

Synthesis of 3-amino-5,6,7,8-tetrahydro-1H-pyrazolo[1,2-a]pyridazin-1-one: C 7.5 ml of ethanol, 1.5 ml of triethylamine and 0.73 ml of 3-amino-3-ethoxyacrylic acid were introduced, with mechanical stirring, into a 25 ml three-necked flask equipped with a condenser and a thermometer. 500 mg of hexahydropyridazine dihydrochloride (compound B) were then added and the mixture was stirred for 3 hours at room temperature.

The insoluble material was filtered off and the solvent was distilled off under vacuum. The solid was taken up in a minimum amount of water, filtered off and dried under vacuum. 0.9 g of a slightly yellow powder was thus obtained.

The NMR ($^1$H 400 MHz and $^{13}$C 100.61 MHz DMSO $d_6$) and mass spectra were in accordance with the expected structure C.

Synthesis of 3-amino-2-nitroso-5,6,7,8-tetrahydro-1H-pyrazolo[1,2-a]pyridazin-1-one: D 20 ml of 35% hydrochloric acid and 1 g of 3-amino-5,6,7,8-tetrahydro-1H-pyrazolo[1,2-a]pyridazin-1-one (compound C) were introduced, with mechanical stirring, into a 50 ml three-necked flask equipped with a condenser and a thermometer.

The mixture was cooled to 0° C. and a solution of 675 mg of sodium nitrite in 5 ml of water was added, while maintaining this temperature. The color of the reaction mixture changed from yellow to orange and a precipitate began to form.

After 30 minutes the reaction was complete, and the orange solid was filtered off on a No. 4 sinter funnel, washed with water and then dried under vacuum. The yield was 78.3%.

The NMR ($^1$H 400 MHz and $^{13}$C 100.61 MHz DMSO $d_6$) and mass spectra were in accordance with the expected structure D.

Synthesis of 2,3-diamino-5,6,7,8-tetrahydro-1H-pyrazolo[1,2-a]pyridazin-1-one hydrochloride: E 1.3 g of 3-amino-2-nitroso-5,6,7,8-tetrahydro-1H-pyrazolo[1,2-a]pyridazin-1-one (compound D) and 250 mg of 5% palladium-on-charcoal were introduced into a 300 ml autoclave containing 250 ml of ethanol. The reduction was performed with stirring at 2000 rpm, at a temperature of 60° C. and under a hydrogen pressure of 6 bar.

After reaction for 2 hours, there was no further consumption of hydrogen, and the medium was cooled to 20° C.

The catalyst was removed by filtration under nitrogen after cooling to room temperature, and the solution was poured into 75 ml of hydrochloric dioxane.

The solution thus obtained was evaporated until a slightly yellow powder was obtained, which was taken up in diisopropyl ether.

The solid was recovered by filtration. After drying under vacuum in the presence of phosphorus pentoxide, 1.1 g of 2,3-diamino-5,6,7,8-tetrahydro-1H-pyrazolo-[1,2-a]pyridazin-1-one dihydrochloride were obtained.

The NMR ($^1$H 400 MHz and $^{13}$C 100.61 MHz DMSO $d_6$) and mass spectra were in accordance with the expected structure E.

Example 7

Synthesis of 4-amino-1,2-diethyl-5-pyrrolidin-1-yl-1,2-dihydropyrazol-3-one hydrochloride

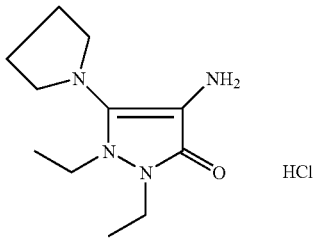

Step 1: Synthesis of 1,2-diethylpyrazolidine-3,5-dione 100 g of diethylhydrazine dihydrochloride (0.63 mol) in 1000 ml of dichloromethane, 85.3 g of malonic acid (0.82 mol; 1.3 eq.), 196 g of hydroxybenzotriazole (1.45 mol; 2.3 eq.) and 278 g of 1-(3-dimethylaminopropyl)-3-ethylcarbodiimide hydrochloride (EDCI; 1.45 mol; 2.3 eq.) were successively introduced, with magnetic stirring, into a 3000 ml three-necked flask under a nitrogen atmosphere, equipped with a thermometer.

The reaction medium was then cooled to a range of from 0° C. to 5° C. 407 g of N,N-diisopropylethylamine (3.14 mol; 520 ml: 5 eq.) were then added slowly thereto. At the end of the addition, the reaction medium, which had become homogeneous, was stirred at room temperature. After leaving overnight at room temperature, the reaction was complete.

The reaction medium was washed with three times 600 ml of deionized water. The organic phase was dried over sodium sulfate, filtered and concentrated under vacuum to give 46 g of crude product. Since the pyrazolidinedione was soluble in aqueous medium, the aqueous phase was thus concentrated to dryness and then taken up in 800 ml of 1N hydrochloric acid solution. The precipitate formed was filtered off and the aqueous phase was extracted with three times 1,300 ml of dichloromethane. The combined organic phases were dried over sodium sulfate, filtered and concentrated under vacuum to give 67.5 g of crude product.

1,2-Diethylpyrazolidine-3,5-dione was thus obtained in the form of a yellow solid in a yield of 40% (39.5 g).

Step 2: Synthesis of 1,2-diethyl-3-chloro-5-pyrazolone 30 g of 1,2-diethylpyrazolidine-3,5-dione (0.19 mol) dissolved in 200 ml of toluene and 35.8 ml of trichlorophosphine oxide (258.9 g; 0.38 mol; 2 eq.) were introduced, under a nitrogen atmosphere, into a 500 ml three-necked flask equipped with a condenser and a magnetic stirrer.

The reaction medium was brought to the reflux temperature of the toluene and the reaction was monitored by TLC (95/5 dichloromethane/methanol). The reaction medium, which was initially in the form of a paste, homogenized as soon as the refluxing started and then became a two-phase mixture.

After refluxing for one hour, the reaction was hydrolysed at 0° C. by very slow addition of 100 ml of deionized water. After settling of the phases, the toluene phase was separated from the aqueous phase. The aqueous phase was washed with 50 ml of toluene and then brought to pH 12 with 184 ml of 35% sodium hydroxide solution. The formation of a precipitate was observed. The aqueous phase was maintained at 100° C. for 10 minutes and the precipitate dissolved. The reaction medium was then in two phases. The brown-colored upper phase was separated out after settling of the phases while hot. This upper phase was dissolved in 200 ml of dichloromethane, washed once with 50 ml of deionized water, dried over sodium sulfate and concentrated under vacuum to give 20.5 g of a brown oil.

A precipitate formed in the lower aqueous phase on cooling to room temperature. After filtering off through a sinter funnel, the precipitate was rinsed with water and the filtrate was extracted with three times 300 ml of dichloromethane. The dichloromethane phase was dried over sodium sulfate and concentrated under vacuum to give 5.5 g of brown crystals.

The oil and the brown crystals were collected, grafted on silica and chromatographed on silica gel (40-60 µm; 2000 g) with an elution gradient:

1) 100 dichloromethane (13 liters)
2) 99.5/0.5 dichloromethane/MeOH (0.8 liter)
3) 99/1 dichloromethane/MeOH (8 liters) expected product+ 15% impurity m=6.6 g
4) 98.5/1.5 dichloromethane/MeOH (35 liters) expected product (14.7 g).

1,2-Diethyl-3-chloro-5-pyrazolone was thus obtained in the form of yellow crystals in a yield of 44%.

Step 3: Synthesis of 1,2-diethyl-5-pyrrolidin-1-yl-1,2-dihydropyrazol-3-one

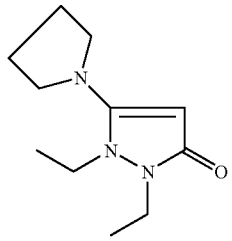

1 g of 5-chloro-1,2-diethyl-1,2-dihydropyrazol-3-one ($5.7 \times 10^{-4}$ mol) was introduced into a 2.5 ml reactor of the Biotage microwave initiator, and 2 ml of pyrrolidine (4.2 eq.) were added thereto.

Operating conditions: microwave at maximum power $\theta = 120°$ C. for 17 minutes.

After 17 minutes, the reaction was complete (monitoring by TLC, eluent: 90/10 $CH_2Cl_2$/MeOH).

5 ml of demineralized water were then added to the reaction medium, and the assembly was then transferred into a separating funnel. The aqueous phase was extracted with four times 10 ml of dichloromethane. The organic phases were then combined and dried over anhydrous sodium sulfate, and then filtered and evaporated to dryness. 1.2 grams of a brown-orange oil were obtained in a yield of 100%.

NMR ($^1$H 400 MHz DMSO $d_6$)

0.81 (1t, 3H), 0.89 (1t, 3H), 1.88 (1m, 1H), 3.22 (1m, 4H), 3.4 (1m, 4H), 4.4 (1s, 1H)

Mass: analysis performed by OpenLynx (FIA/MS).

The mass mainly detected was in accordance with the expected structure: M=20.

Step 4: Synthesis of 1,2-diethyl-4-nitroso-5-pyrrolidin-1-yl-1,2-dihydro-3H-pyrazol-3-one

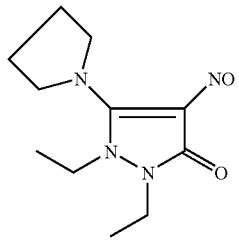

1.2 g of 1,2-diethyl-5-pyrrolidin-1-yl-1,2-dihydropyrazol-3-one were introduced into a fully equipped 25 ml three-necked flask and dissolved in a mixture composed of 0.84 ml of 37% hydrochloric acid and 4 ml of demineralized water.

The reaction medium was cooled to a range of from 0° C. to 5° C. using a bath of ice-water.

A solution composed of 400 mg of sodium nitrite ($5.7 \times 10^{-4}$ mol) dissolved in 0.6 ml of demineralized water was then added dropwise.

The reaction medium immediately turned bright red as soon as the first drop of the above mixture was added.

After one hour, the reaction was complete.

The pH was adjusted to about 7-8 with 30% sodium hydroxide solution and the reaction medium was then transferred into a separating funnel. The aqueous phase was extracted with 4 times 10 ml of dichloromethane. The organic phases were combined and dried over anhydrous sodium sulfate and then evaporated to dryness. 1.2 grams of a turquoise-blue powder were obtained in a yield of 89.6%.

The NMR ($^1$H 400 MHz DMSO $d_6$) and mass spectra were in accordance with the expected structure.

NMR ($^1$H 400 MHz DMSO $d_6$) 0.94 (1t, 3H), 1 (1t, 3H), 2.05 (1m, 4H), 3.51 (1q, 4H), 3.76 (1q, 4H), 3.94 (1m, 4H)

Analysis performed by OpenLynx (FIA/MS).

The mass mainly detected was in accordance with the expected structure. M=238.

Step 5: Synthesis of 4-amino-1,2-diethyl-5-pyrrolidin-1-yl-1,2-dihydropyrazol-3-one hydrochloride 4 grams of zinc powder (0.06 mol) were introduced into 300 ml of absolute ethanol in a fully equipped 500 ml three-necked flask, and 1 ml of acetic acid was added thereto.

The reaction medium was heated to 40° C. and 1.15 g ($4.8 \times 10^{-3}$ mol) of 1,2-diethyl-4-nitroso-5-pyrrolidin-1-yl-1,2-dihydro-3H-pyrazol-3-one were then introduced in spatula portions. 4 ml of acetic acid were finally introduced milliliter by milliliter and the medium was brought to reflux. The medium was fully soluble and colorless. After 30 minutes, the reaction was complete on TLC according to the eluent 90/10 ethyl acetate/MeOH.

The reaction medium was cooled and then filtered on a sinter funnel containing a bed of Celite 545. The mother liquors were filtered into a round-bottomed flask containing 2.5 ml of cooled 5N hydrochloric isopropanol. The mixture was then evaporated to dryness. The product obtained was a pink powder that was in accordance by NMR and Mass.

NMR ($^1$H 400 MHz DMSO $d_6$) 0.79 (1t, 3H), 0.96 (1t, 3H), 1.87 (1m, 4H), 3.49 (1q, 2H), 3.59 (1m, 6H)

FIA/MS analysis performed via OpenLynx.

The quasimolecular ions $[M+H]^+$, $[M+Na]^+$, $[2M+H]^+$, $[2M+Na]^+$ of the expected base $C_{11}H_{20}N_4O$ were mainly detected.

By repeating the above steps with the appropriate reagents, 4-amino-5-[3-(dimethylamino)pyrrolidin-1-yl]-1,2-diethyl-1,2-dihydro-3H-pyrazol-3-one hydrochloride may be obtained.

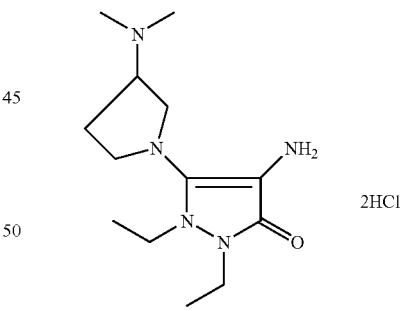

EXAMPLES OF DYEING

Example 1

Composition 1 below was prepared:

| | |
|---|---|
| Mixture of linear $C_{18}$ to $C_{24}$ alcohols [7/57/30/6 $C_{18}/C_{20}/C_{22}/C_{24}$, alcohol content > 95%] | 3 g |
| Oxyethylenated (2 EO) stearyl alcohol | 4.5 g |
| Oxyethylenated (21 EO) stearic acid | 1.75 g |
| Oleyl alcohol | 2.6 g |

-continued

| | |
|---|---|
| Fatty-chain cationic polyurethane obtained from the condensation of N,N-dimethylethanolamine 1,3-bis(isocyanatomethylcyclohexane) quaternized with N,N-dimethylethanolamine polyoxyethylene bromodecane, with a molecular weight of 10 000 (MEXOMERE PAR) | 0.2 g AM |
| Crosslinked polyacrylic acid | 0.4 g |
| Hydroxypropylmethylcellulose | 0.2 g |
| Stearic acid monoethanolamide | 3 g |
| Merquat 100 as an aqueous 40% solution | 4 g |
| Cationic polymer* | 2 g AM |
| Propylene glycol | 2 g |
| Sodium metabisulfite | 0.71 g |
| EDTA | 0.2 g |
| tert-Butylhydroquinone | 0.3 g |
| 2,3-Diamino-6,7-dihydro-1H,5H-pyrazolo[1,2-a]pyrazol-1-one, HCl | 1.362 g |
| 2-Methyl-5-hydroxyethylaminophenol | 1.002 g |
| Monoethanolamine | 1 g |
| Aqueous ammonia containing 20% $NH_3$ | 11 g |
| Fragrance | qs |
| Demineralized water | qs 100 g |

*Cationic polymer comprising the sequence of units:

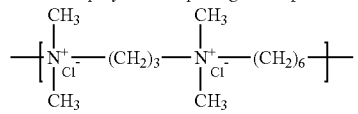

Mode of Application

At the time of use, Composition 1 was mixed with 1.5 times its volume of 25-volumes hydrogen peroxide solution of pH 3. A final pH of 9.8 was obtained.

The mixture obtained was applied to locks of natural grey hair containing 90% white hairs, in a proportion of 30 g of mixture per 3 g of hair. After a leave-in time of 30 minutes at room temperature, the locks were rinsed, washed with a standard shampoo, rinsed again and then dried.

The hair coloration was evaluated visually:

| | Tone depth | Tint |
|---|---|---|
| Composition 1 | Dark blonde | Coppery |

Example 2

Composition 2 below was prepared:

| | |
|---|---|
| Mixture of linear $C_{18}$ to $C_{24}$ alcohols [7/57/30/6 $C_{18}/C_{20}/C_{22}/C_{24}$, alcohol content > 95%] | 3 g |
| Oxyethylenated (2 EO) stearyl alcohol | 4.5 g |
| Oxyethylenated (21 EO) stearic acid | 1.75 g |
| Oleyl alcohol | 2.6 g |
| Aculyn 44 sold by the company Röhm & Haas | 0.2 g AM |
| Crosslinked polyacrylic acid | 0.4 g |
| Hydroxypropylmethylcellulose | 0.2 g |
| Stearic acid monoethanolamide | 3 g |
| Merquat 100 as an aqueous 40% solution | 4 g |
| Cationic polymer* | 2 g AM |
| Propylene glycol | 2 g |
| Sodium metabisulfite | 0.71 g |
| EDTA | 0.2 g |
| tert-Butylhydroquinone | 0.3 g |
| 2,3-Diamino-6,7-dihydro-1H,5H-pyrazolo[1,2-a]pyrazol-1-one, HCl | 1.362 g |
| 2-Methyl resorcinol | 0.744 g |
| Monoethanolamine | 1 g |
| Aqueous ammonia containing 20% $NH_3$ | 11 g |
| Fragrance | qs |
| Demineralized water | qs 100 g |

*See Example 1

Mode of Application

At the time of use, composition 2 was mixed with 1.5 times its volume of 25-volumes hydrogen peroxide solution of pH 3. A final pH of 9.8 was obtained.

The mixture obtained was applied to locks of natural grey hair containing 90% white hairs, in a proportion of 30 g of mixture per 3 g of hair. After a leave-in time of 30 minutes at room temperature, the locks were rinsed, washed with a standard shampoo, rinsed again and then dried.

The hair coloration was evaluated visually.

| | Tone depth | Tint |
|---|---|---|
| Composition 2 | Light blonde | Iridescent golden coppery |

Example 3

Composition 3 below was prepared:

| | |
|---|---|
| Mixture of linear $C_{18}$ to $C_{24}$ alcohols [7/57/30/6 $C_{18}/C_{20}/C_{22}/C_{24}$, alcohol content >95%] | 3 g |
| Oxyethylenated (2 EO) stearyl alcohol | 4.5 g |
| Oxyethylenated (21 EO) stearic acid | 1.75 g |
| Oleyl alcohol | 2.6 g |
| Fatty-chain cationic polyurethane obtained from the condensation of N,N-dimethylethanolamine 1,3-bis(isocyanatomethylcyclohexane) quaternized with N,N-dimethylethanolamine polyoxyethylene bromodecane, with a molecular weight of 10,000 (MEXOMERE PAR) | 0.2 g AM |
| Crosslinked polyacrylic acid | 0.4 g |
| Hydroxypropylmethylcellulose | 0.2 g |
| Stearic acid monoethanolamide | 3 g |
| Merquat 100 as an aqueous 40% solution | 4 g |
| Cationic polymer* | 2 g AM |
| Propylene glycol | 2 g |
| Sodium metabisulfite | 0.71 g |
| EDTA | 0.2 g |
| tert-Butylhydroquinone | 0.3 g |
| 4-Amino-1,2-diethyl-5-pyrrolidin-1-yl-1,2-dihydro-3H-pyrazol-3-one, HCl | 1.827 g |
| 1-Methyl-2-hydroxy-4-aminobenzene | 0.861 g |
| Monoethanolamine | 1 g |
| Aqueous ammonia containing 20% $NH_3$ | 11 g |
| Fragrance | qs |
| Demineralized water | qs 100 g |

*See Example 1

Mode of Application

At the time of use, composition 3 was mixed with 1.5 times its volume of 25-volumes hydrogen peroxide solution of pH 3. A final pH of 9.8 was obtained.

The mixture obtained was applied to locks of natural grey hair containing 90% white hairs, in a proportion of 30 g of mixture per 3 g of hair. After a leave-in time of 30 minutes at room temperature, the locks were rinsed, washed with a standard shampoo, rinsed again and then dried.

The hair coloration was evaluated visually:

|  | Tone depth | Tint |
| --- | --- | --- |
| Composition 3 | Blonde | Iridescent red |

Example 4

Composition 4 below was prepared:

| | |
| --- | --- |
| Mixture of linear $C_{18}$ to $C_{24}$ alcohols [7/57/30/6 $C_{18}/C_{20}/C_{22}/C_{24}$, alcohol content >95%] | 3 g |
| Oxyethylenated (2 EO) stearyl alcohol | 4.5 g |
| Oxyethylenated (21 EO) stearic acid | 1.75 g |
| Oleyl alcohol | 2.6 g |
| Aculyn 44 sold by the company Röhm & Haas | 0.2 g AM |
| Crosslinked polyacrylic acid | 0.4 g |
| Hydroxypropylmethylcellulose | 0.2 g |
| Stearic acid monoethanolamide | 3 g |
| Merquat 100 as an aqueous 40% solution | 4 g |
| Cationic polymer* | 2 g AM |
| Propylene glycol | 2 g |
| Sodium metabisulfite | 0.71 g |
| EDTA | 0.2 g |
| tert-Butylhydroquinone | 0.3 g |
| 2,3-Diamino-6-hydroxy-6,7-dihydro-1H,5H-pyrazolo[1,2-a]pyrazol-1-one dimethanesulfonate | 1.81 g |
| 5-Amino-6-chloro-o-cresol | 0.787 g |
| Monoethanolamine | 1 g |
| Aqueous ammonia containing 20% $NH_3$ | 11 g |
| Fragrance | qs |
| Demineralized water | qs 100 g |

*See Example 1

Mode of Application

At the time of use, composition 4 was mixed with 1.5 times its volume of 25-volumes hydrogen peroxide solution of pH 3. A final pH of 9.8 was obtained.

The mixture obtained was applied to locks of natural grey hair containing 90% white hairs, in a proportion of 30 g of mixture per 3 g of hair. After a leave-in time of 30 minutes at room temperature, the locks were rinsed, washed with a standard shampoo, rinsed again and then dried.

The hair coloration was evaluated visually:

|  | Tone depth | Tint |
| --- | --- | --- |
| Composition 4 | Blonde | Strong coppery |

Example 5

Composition 5 below was prepared:

| | |
| --- | --- |
| Mixture of linear $C_{18}$ to $C_{24}$ alcohols [7/57/30/6 $C_{18}/C_{20}/C_{22}/C_{24}$, alcohol content > 95%] | 3 g |
| Oxyethylenated (2 EO) stearyl alcohol | 4.5 g |
| Oxyethylenated (21 EO) stearic acid | 1.75 g |
| Oleyl alcohol | 2.6 g |
| Fatty-chain cationic polyurethane obtained from the condensation of N,N-dimethylethanolamine 1,3-bis(isocyanatomethylcyclohexane) quaternized with N,N-dimethylethanolamine polyoxyethylene bromodecane, with a molecular weight of 10 000 (MEXOMERE PAR) | 0.2 g AM |
| Crosslinked polyacrylic acid | 0.4 g |
| Hydroxypropylmethylcellulose | 0.2 g |
| Stearic acid monoethanolamide | 3 g |
| Merquat 100 as an aqueous 40% solution | 4 g |
| Cationic polymer* | 2 g AM |
| Propylene glycol | 2 g |
| Sodium metabisulfite | 0.71 g |
| EDTA | 0.2 g |
| tert-Butylhydroquinone | 0.3 g |
| 2,3-Diamino-6,7-dihydro-1H,5H-pyrazolo[1,2-a]pyrazol-1-one, HCl | 1.73 g |
| 1-β-Hydroxyethyloxy-2,4-diaminobenzene dihydrochloride 2,4-diaminophenoxy ethanol HCl | 1.2 g |
| Monoethanolamine | 1 g |
| Citric acid | 0.15 g |
| Fragrance | qs |
| Demineralized water | qs 100 g |

*Cationic polymer comprising the sequence of units:

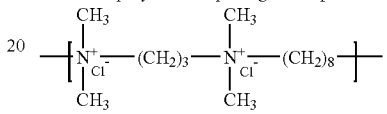

Mode of Application

At the time of use, composition 5 was mixed with 1.5 times its volume of 25-volumes hydrogen peroxide solution of pH 3. A final pH of 6.1 was obtained.

The mixture obtained was applied to locks of natural grey hair containing 90% white hairs, in a proportion of 30 g of mixture per 3 g of hair. After a leave-in time of 30 minutes at room temperature, the locks were rinsed, washed with a standard shampoo, rinsed again and then dried.

The hair coloration was evaluated visually:

|  | Tone depth | Tint |
| --- | --- | --- |
| Composition 5 | Blonde | Coppery red |

Example 6

Composition 6 below was prepared:

| | |
| --- | --- |
| Mixture of linear $C_{18}$ to $C_{24}$ alcohols [7/57/30/6 $C_{18}/C_{20}/C_{22}/C_{24}$, alcohol content >95%] | 3 g |
| Oxyethylenated (2 EO) stearyl alcohol | 4.5 g |
| Oxyethylenated (21 EO) stearic acid | 1.75 g |
| Oleyl alcohol | 2.6 g |
| Aculyn 44 sold by the company Röhm & Haas | 0.2 g AM |
| Crosslinked polyacrylic acid | 0.4 g |
| Hydroxypropylmethylcellulose | 0.2 g |
| Stearic acid monoethanolamide | 3 g |
| Merquat 100 as an aqueous 40% solution | 4 g |
| Cationic polymer* | 2 g AM |
| Propylene glycol | 2 g |
| Sodium metabisulfite | 0.71 g |
| EDTA | 0.2 g |
| tert-Butylhydroquinone | 0.3 g |
| 2,3-Diamino-6,7-dihydro-1H,5H-pyrazolo[1,2-a]pyrazol-1-one, HCl | 2.08 g |
| 1-Hydroxy-3-aminobenzene | 0.65 g |
| Monoethanolamine | 1 g |
| Citric acid | 0.15 g |
| Fragrance | qs |
| Demineralized water | qs 100 g |

*See Example 5

Mode of Application

At the time of use, composition 6 was mixed with 1.5 times its volume of 25-volumes hydrogen peroxide solution of pH 3. A final pH of 6.4 was obtained.

The mixture obtained was applied to locks of natural grey hair containing 90% white hairs, in a proportion of 30 g of mixture per 3 g of hair. After a leave-in time of 30 minutes at room temperature, the locks were rinsed, washed with a standard shampoo, rinsed again and then dried.

The hair coloration was evaluated visually.

|  | Tone depth | Tint |
| --- | --- | --- |
| Composition 6 | Light blonde | Coppery red |

What is claimed is:

1. A composition for dyeing keratin fibers, comprising, in a suitable medium:
    at least one oxidation base chosen from diamino-N,N-dihydropyrazolone compounds of formula (I), and addition salts thereof:

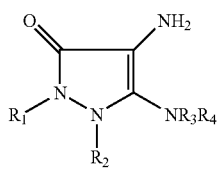

in which:
$R_1$, $R_2$, $R_3$ and $R_4$, which may be identical or different, are chosen from:
linear and branched $C_1$-$C_{10}$ alkyl radicals optionally substituted with at least one radical chosen from $OR_5$, $NR_6R_7$, carboxyl radicals, sulfonic radicals, carboxamido radicals $CONR_6R_7$, sulfonamido radicals $SO_2NR_6R_7$, heteroaryls and aryls optionally substituted with at least one group chosen from ($C_1$-$C_4$)alkyl, hydroxyl, $C_1$-$C_2$ alkoxy, amino and (di)($C_1$-$C_2$)alkylamino groups;
aryl radicals optionally substituted with at least one radical chosen from ($C_1$-$C_4$)alkyl, hydroxyl, $C_1$-$C_2$ alkoxy, amino and (di)($C_1$-$C_2$)alkylamino radicals;
5- or 6-membered heteroaryl radicals, optionally substituted with at least one radical chosen from ($C_1$-$C_4$)alkyl and ($C_1$-$C_2$)alkoxy radicals;
$R_3$ and $R_4$ may also be a hydrogen atom;
$R_5$, $R_6$ and $R_7$, which may be identical or different, are chosen from:
hydrogen atoms;
linear and branched $C_1$-$C_4$ alkyl radicals optionally substituted with at least one radical chosen from hydroxyl, $C_1$-$C_2$ alkoxy, carboxamido $CONR_8R_9$, sulfonyl $SO_2R_8$ and aryl radicals optionally substituted with at least one radical chosen from ($C_1$-$C_4$)alkyl, hydroxyl, $C_1$-$C_2$ alkoxy, amino and (di)($C_1$-$C_2$)alkylamino radicals; aryl optionally substituted with at least one radical chosen from ($C_1$-$C_4$)alkyl, hydroxyl, $C_1$-$C_2$ alkoxy, amino and (di)($C_1$-$C_2$)alkylamino radicals;
$R_6$ and $R_7$, which may be identical or different, may also be chosen from carboxamido radicals $CONR_8R_9$; and sulfonyl radicals $SO_2R_8$;
$R_8$ and $R_9$, which may be identical or different, are chosen from hydrogen atoms; linear and branched $C_1$-$C_4$ alkyl radicals optionally substituted with at least one radical chosen from hydroxyl radicals and $C_1$-$C_2$ alkoxy radicals;
$R_1$ and $R_2$, on the one hand, and $R_3$ and $R_4$, on the other hand, may form, with the nitrogen atom(s) to which they are attached, a saturated or unsaturated 5- to 7-membered heterocycle optionally substituted with at least one entity chosen from halogen atoms and from amino, (di)($C_1$-$C_4$)alkylamino, hydroxyl, carboxyl, carboxamido and ($C_1$-$C_2$)alkoxy radicals, and from $C_1$-$C_4$ alkyl radicals optionally substituted with at least one radical chosen from hydroxyl, amino, (di)alkylamino, alkoxy, carboxyl and sulfonyl radicals;
$R_3$ and $R_4$ may also form, together with the nitrogen atom to which they are attached, a 5- or 7-membered heterocycle, the carbon atoms of which may be replaced with an optionally substituted oxygen or nitrogen atom;
at least one coupler; and
at least one associative polymer of polyurethane type.

2. A composition according to claim 1, in which $R_1$ and $R_2$ are independently chosen from $C_1$-$C_6$ alkyl radicals optionally substituted with at least one radical chosen from hydroxyl, ($C_1$-$C_2$)alkoxy, amino and (di)($C_1$-$C_2$)alkylamino radicals; and from phenyl, methoxyphenyl, ethoxyphenyl and benzyl radicals.

3. A composition according to claim 2, in which $R_1$ and $R_2$ are independently chosen from methyl, ethyl, 2-hydroxyethyl, 3-hydroxypropyl, 2-hydroxypropyl and phenyl radicals.

4. A composition according to claim 1, in which $R_1$ and $R_2$ form, together with the nitrogen atoms to which they are attached, a saturated or unsaturated, optionally substituted 5- or 6-membered ring.

5. A composition according to claim 1, in which $R_1$ and $R_2$ form, together with the nitrogen atoms to which they are attached, a pyrazolidine or pyridazolidine ring, optionally substituted with at least one radical chosen from $C_1$-$C_4$ alkyl, hydroxyl, ($C_1$-$C_2$)alkoxy, carboxyl, carboxamido, amino and (di)($C_1$-$C_2$)alkylamino radicals.

6. A composition according to claim 4, in which $R_1$ and $R_2$ form, together with the nitrogen atoms to which they are attached, a pyrazolidine or pyridazolidine ring.

7. A composition according to claim 1, in which $R_3$ and $R_4$ are independently chosen from hydrogen atoms; linear and branched $C_1$-$C_6$ alkyl radicals optionally substituted with at least one radical chosen from hydroxyl, ($C_1$-$C_2$)alkoxy, amino and (di)($C_1$-$C_2$)alkylamino radicals; phenyl radicals optionally substituted with at least one radical chosen from hydroxyl, amino and ($C_1$-$C_2$)alkoxy radicals.

8. A composition according to claim 7, in which $R_3$ and $R_4$ are independently chosen from hydrogen atoms and methyl, ethyl, isopropyl, 2-hydroxyethyl, 3-hydroxypropyl, 2-hydroxypropyl and 2-carboxyethyl radicals.

9. A composition according to claim 8, in which $R_3$ and $R_4$ each are a hydrogen atom.

10. A composition according to claim 1, in which $R_3$ and $R_4$ form, together with the nitrogen atom to which they are attached, a 5- or 7-membered ring chosen from pyrrolidine, piperidine, homopiperidine, piperazine and homopiperazine heterocycles; said rings optionally being substituted with at least one radical chosen from hydroxyl, amino, (di)($C_1$-$C_2$) alkylamino, carboxyl, carboxamido and $C_1$-$C_4$ alkyl radicals optionally substituted with at least one radical chosen from hydroxyl, amino and $C_1$-$C_2$ (di)alkylamino radicals.

11. A composition according to claim 1, in which $R_3$ and $R_4$ form, together with the nitrogen atom to which they are attached, a 5- or 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethylpyrrolidine, 2-carboxamidopyrrolidine, 3-hydroxy-2-carboxamidopyrrolidine, 2-(diethylcarboxamido)pyrrolidine, 2-hydroxymethylpyrrolidine, 3,4-dihydroxy-2-hydroxymethylpyrrolidine, 3-hydroxypyrrolidine, 3,4-dihydroxypyrrolidine, 3-aminopyrrolidine, 3-methylaminopyrrolidine, 3-dimethylaminopyrrolidine, 4-amino-3-hydroxypyrrolidine, 3-hydroxy-4-(2-hydroxyethyl)aminopyrrolidine, piperidine, 2,6-dimethylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamidohomopiperidine, homopiperazine, N-methylhomopiperazine and N-(2-hydroxyethyl)homopiperazine.

12. A composition according to claim 11, in which $R_3$ and $R_4$ form, together with the nitrogen atom to which they are attached, a 5- or 7-membered ring chosen from pyrrolidine, 3-hydroxypyrrolidine, 3-aminopyrrolidine, 3-dimethylaminopyrrolidine, pyrrolidine-2-carboxylic acid, 3-hydroxypyrrolidine-2-carboxylic acid, piperidine, hydroxypiperidine, homopiperidine, diazepane, N-methylhomopiperazine and N-β-hydroxyethylhomopiperazine.

13. A composition according to claim 12, in which $R_3$ and $R_4$ form, together with the nitrogen atom to which they are attached, a 5-membered ring chosen from pyrrolidine, 3-hydroxypyrrolidine, 3-aminopyrrolidine and 3-dimethylaminopyrrolidine.

14. A composition according to claim 1, in which the at least one oxidation base chosen from diamino-N,N-dihydropyrazolone derivatives of formula (I), and addition salts thereof, is chosen from:

2,3-diamino-6,7-dihydro-1H,5H-pyrazolo[1,2-a]pyrazol-1-one;
2-amino-3-ethylamino-6,7-dihydro-1H,5H-pyrazolo[1,2-a]pyrazol-1-one;
2-amino-3-isopropylamino-6,7-dihydro-1H,5H-pyrazolo[1,2-a]pyrazol-1-one;
2-amino-3-(pyrrolidin-1-yl)-6,7-dihydro-1H,5H-pyrazolo[1,2-a]pyrazol-1-one;
4,5-diamino-1,2-dimethyl-1,2-dihydropyrazol-3-one;
4,5-diamino-1,2-diethyl-1,2-dihydropyrazol-3-one;
4,5-diamino-1,2-di-(2-hydroxyethyl)-1,2-dihydropyrazol-3-one;
2-amino-3-(2-hydroxyethyl)amino-6,7-dihydro-1H,5H-pyrazolo[1,2-a]pyrazol-1-one;
2-amino-3-dimethylamino-6,7-dihydro-1H,5H-pyrazolo[1,2-a]pyrazol-1-one;
2,3-diamino-5,6,7,8-tetrahydro-1H,6H-pyridazino[1,2-a]pyrazol-1-one;
4-amino-1,2-diethyl-5-pyrrolidin-1-yl-1,2-dihydropyrazol-3-one;
4-amino-5-(3-dimethylaminopyrrolidin-1-yl)-1,2-diethyl-1,2-dihydropyrazol-3-one; and
2,3-diamino-6-hydroxy-6,7-dihydro-1H,5H-pyrazolo[1,2-a]pyrazol-1-one.

15. A composition according to claim 1, in which the at least one coupler is chosen from meta-phenylenediamines, meta-aminophenols, meta-diphenols, naphthalene-based couplers, heterocyclic couplers, and the addition salts thereof.

16. A composition according to claim 15, in which the at least one coupler is chosen from 2-methyl-5-aminophenol, 5-N-(β-hydroxyethyl)amino-2-methylphenol, 6-chloro-2-methyl-5-aminophenol, 3-aminophenol, 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-dimethylaminobenzene, sesamol, 1-β-hydroxyethylamino-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and the acid-addition salts thereof.

17. A composition according to claim 1, in which the amount of the at least one coupler, or of each of the couplers when there is more than one, ranges from 0.001% to 10% by weight relative to the total weight of the dye composition.

18. A composition according to claim 1, in which the at least one associative polyurethane polymer is chosen from cationic, anionic and non-ionic associative polyurethane polymers.

19. A composition according to claim 18, in which the at least one associative polyurethane polymer is a cationic polyurethane and is chosen from the compounds of formula (II)

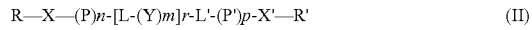

R—X—(P)n-[L-(Y)m]r-L'-(P')p-X'—R'      (II)

in which:
R and R', which may be identical or different, are chosen from hydrophobic groups and hydrogen atoms;
X and X', which may be identical or different, are chosen from groups comprising an amine functional group optionally bearing a hydrophobic group, and from groups L";
L, L' and L", which may be identical or different, are chosen from groups derived from a diisocyanate;
P and P', which may be identical or different, are chosen from groups comprising an amine functional group optionally bearing a hydrophobic group;
Y is a hydrophilic group;
r is an integer ranging from 1 to 100;
n, m and p each range, independently of each other, from 0 to 1,000; the molecule containing at least one quaternary amine functional group or quaternized amine functional group and at least one hydrophobic group.

20. A composition according to claim 19, in which r is an integer ranging from 1 to 25.

21. A composition according to claim 19, in which the only hydrophobic groups are the groups R and R' at the ends of the chain.

22. A composition according to claim 19, in which R and R' both independently are a hydrophobic group, X and X' each are a group L", n and p range from 1 to 1,000 and L, L', L", P, P', Y and m have the meaning indicated in claim 19.

23. A composition according to claim 19, in which R and R' both independently are a hydrophobic group, X and X' each are a group L", n and p are 0, and L, L', L", Y and m have the meaning indicated in claim 19.

24. A composition according to claim 19, in which R and R' both independently are a hydrophobic group, X and X' both independently are a group comprising a quaternary amine, n and p are 0, and L, L', Y and m have the meaning indicated in claim 19.

25. A composition according to claim 19, in which the at least one cationic polyurethane associative polymer has a number-average molecular mass ranging from 400 to 500,000.

26. A composition according to claim 19, in which R and R' are each independently chosen from radicals and polymers having a linear or branched, saturated or unsaturated hydrocarbon-based chain, which may comprise at least one heteroatom, and from radicals comprising a perfluoro or silicone chain.

27. A composition according to claim 26, in which said heteroatom is chosen from P, O, N, and S.

28. A composition according to claim 19, in which X and/or X' are independently chosen from one of the following formulae:

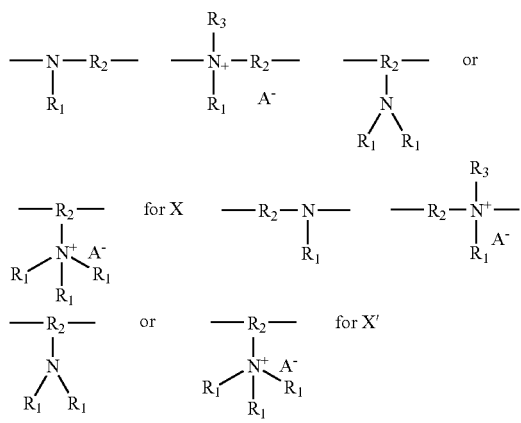

in which:

R$_2$ is chosen from linear and branched alkylene radicals comprising from 1 to 20 carbon atoms, optionally comprising a saturated or unsaturated ring, and from arylene radicals, at least one of the carbon atoms possibly being replaced with a heteroatom chosen from N, S, O and P;

R$_1$ and R$_3$, which may be identical or different, are chosen from linear are branched C$_1$-C$_{30}$ alkyl and alkenyl radicals and aryl radicals, which may comprise at least one heteroatom chosen from N, S, O and P;

A$^-$ is a physiologically acceptable counterion.

29. A composition according to claim 19, in which the groups L, L' and L" are independently chosen from groups of formula:

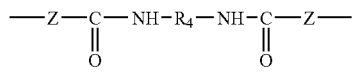

in which:

Z is chosen from —O—, —S— and —NH—; and R$_4$ is chosen from linear and branched alkylene radicals comprising from 1 to 20 carbon atoms, optionally comprising a saturated or unsaturated ring, and from arylene radicals, which may comprise 1, 2 or 3 heteroatoms.

30. A composition according to claim 19, in which the groups P and P', which may be identical or different, are each chosen from at least one of the following formulae:

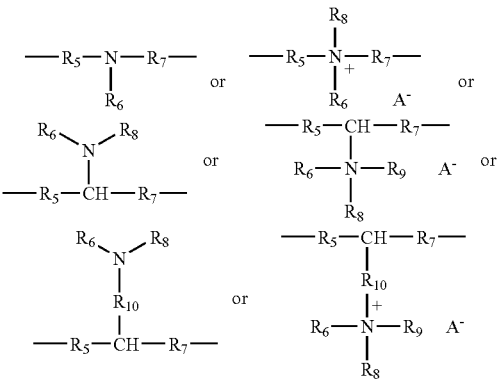

in which:

R$_5$ and R$_7$, which may be identical or different, are chosen from linear and branched alkylene radicals comprising from 1 to 20 carbon atoms, optionally comprising a saturated or unsaturated ring, and from arylene radicals, at least one of the carbon atoms possibly being replaced with a heteroatom chosen from N, S, O and P;

R$_6$, R$_8$ and R$_9$, which may be identical or different, are chosen from linear and branched C$_1$-C$_{30}$ alkyl and alkenyl radicals and aryl radicals, which may comprise at least one heteroatom chosen from N, S, O and P;

R$_{10}$ is a linear or branched, optionally unsaturated alkylene group, which may comprise at least one heteroatom chosen from N, O, S and P; and A$^-$ is a physiologically acceptable counterion.

31. A composition according to claim 19, in which Y is chosen from groups derived from ethylene glycol, diethylene glycol or propylene glycol, and from groups derived from a polymer chosen from polyethers, sulfonated polyesters and sulfonated polyamides.

32. A composition according to claim 18, in which the at least one polyurethane associative polymer is a fatty-chain cationic polyurethane associative polymer obtained from the condensation of N,N-dimethylethanolamine 1,3-bis(isocyanatomethylcyclohexane) quaternized with N,N-dimethylethanolamine polyoxyethylene bromodecane with a molecular weight of 10,000.

33. A composition according to claim 18, in which the at least one polyurethane associative polymer is a nonionic polyurethane-polyether associative polymer that may be obtained by polycondensation of at least three compounds comprising (i) at least one polyethylene glycol comprising from 150 to 180 mol of ethylene oxide, (ii) stearyl alcohol or decyl alcohol, and (iii) at least one diisocyanate.

34. A composition according to claim 33, in which the nonionic associative polyurethane is chosen from polycondensates of polyethylene glycol comprising 150 to 180 mol of ethylene oxide, stearyl alcohol and methylenebis(4-cyclohexyl isocyanate) and from polycondensates of polyethylene glycol comprising 150 to 180 mol of ethylene oxide, decyl alcohol and methylenebis(4-cyclohexyl isocyanate).

35. A composition according to claim 1, in which the at least one polyurethane associative polymer is present in an amount ranging from 0.01% to 10% by weight relative to the total weight of the dye composition.

36. A composition according to claim 1, further comprising at least one additional oxidation base chosen from para-phenylenediamines, bis(phenyl)alkylenediamines, para-aminophenols, bis-para-aminophenols, ortho-aminophenols, ortho-phenylenediamines, heterocyclic bases other than the derivatives of formula (I), and the addition salts thereof.

37. A composition according to claim 1, in which the amount of the at least one oxidation base, or each of the oxidation bases when more than one is present, ranges from 0.001% to 10% by weight relative to the total weight of the dye composition.

38. A composition according to claim 1, further comprising at least one oxidizing agent.

39. A process for dyeing keratin fibers, comprising applying to said keratin fibers a dyeing composition, in the presence of at least one oxidizing agent, for a time sufficient to develop a desired coloration,
wherein said dyeing composition comprises, in a suitable medium:
at least one oxidation base chosen from diamino-N,N-dihydropyrazolone compounds of formula (I), and addition salts thereof:

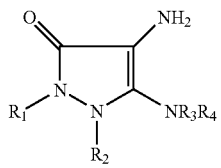
(I)

in which:
$R_1$, $R_2$, $R_3$ and $R_4$, which may be identical or different, are chosen from:
linear and branched $C_1$-$C_{10}$ alkyl radicals optionally substituted with at least one radical chosen from $OR_5$, $NR_6R_7$, carboxyl radicals, sulfonic radicals, carboxamido radicals $CONR_6R_7$, sulfonamido radicals $SO_2NR_6R_7$, heteroaryls and aryls optionally substituted with at least one group chosen from ($C_1$-$C_4$)alkyl, hydroxyl, $C_1$-$C_2$ alkoxy, amino and (di)($C_1$-$C_2$)alkylamino groups;
aryl radicals optionally substituted with at least one radical chosen from ($C_1$-$C_4$)alkyl, hydroxyl, $C_1$-$C_2$ alkoxy, amino and (di)($C_1$-$C_2$)alkylamino radicals;
5- or 6-membered heteroaryl radicals, optionally substituted with at least one radical chosen from ($C_1$-$C_4$)alkyl and ($C_1$-$C_2$)alkoxy radicals;
$R_3$ and $R_4$ may also be a hydrogen atom;
$R_5$, $R_6$ and $R_7$, which may be identical or different, are chosen from:
hydrogen atoms;
linear and branched $C_1$-$C_4$ alkyl radicals optionally substituted with at least one radical chosen from hydroxyl, $C_1$-$C_2$ alkoxy, carboxamido $CONR_8R_9$, sulfonyl $SO_2R_8$ and aryl radicals optionally substituted with at least one radical chosen from ($C_1$-$C_4$)alkyl, hydroxyl, $C_1$-$C_2$ alkoxy, amino and (di)($C_1$-$C_2$)alkylamino radicals; aryl optionally substituted with at least one radical chosen from ($C_1$-$C_4$)alkyl, hydroxyl, $C_1$-$C_2$ alkoxy, amino and (di)($C_1$-$C_2$)alkylamino radicals;
$R_6$ and $R_7$, which may be identical or different, may also be chosen from carboxamido radicals $CONR_8R_9$; and sulfonyl radicals $SO_2R_8$;
$R_8$ and $R_9$, which may be identical or different, are chosen from hydrogen atoms; linear and branched $C_1$-$C_4$ alkyl radicals optionally substituted with at least one radical chosen from hydroxyl radicals and $C_1$-$C_2$ alkoxy radicals;

$R_1$ and $R_2$, on the one hand, and $R_3$ and $R_4$, on the other hand, may form, with the nitrogen atom(s) to which they are attached, a saturated or unsaturated 5- to 7-membered heterocycle optionally substituted with at least one entity chosen from halogen atoms, and amino, (di)($C_1$-$C_4$)alkylamino, hydroxyl, carboxyl, carboxamido and ($C_1$-$C_2$)alkoxy radicals, and from $C_1$-$C_4$ alkyl radicals optionally substituted with at least one radical chosen from hydroxyl, amino, (di)alkylamino, alkoxy, carboxyl and sulfonyl radicals;
$R_3$ and $R_4$ may also form, together with the nitrogen atom to which they are attached, a 5- or 7-membered heterocycle, the carbon atoms of which may be replaced with an optionally substituted oxygen or nitrogen atom;
at least one coupler; and
at least one associative polyurethane polymer.

40. A process according to claim 39, in which the at least one oxidizing agent is chosen from hydrogen peroxide, urea peroxide, alkali metal bromates, persalts, peracids and oxidase enzymes.

41. A multi-compartment device, comprising
at least one first compartment comprising a dyeing composition and
at least one second compartment comprising at least one oxidizing agent, wherein said dyeing composition comprises, in a suitable medium:
at least one oxidation base chosen from a diamino-N,N-dihydropyrazolone compound of formula (I), and addition salts thereof:

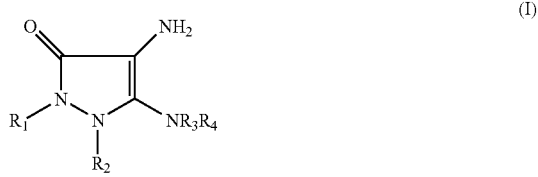
(I)

in which:
$R_1$, $R_2$, $R_3$ and $R_4$, which may be identical or different, are chosen from:
linear and branched $C_1$-$C_{10}$ alkyl radicals optionally substituted with at least one radical chosen from $OR_5$, $NR_6R_7$, carboxyl radicals, sulfonic radicals, carboxamido radicals $CONR_6R_7$, sulfonamido radicals $SO_2NR_6R_7$, heteroaryls and aryls optionally substituted with at least one group chosen from ($C_1$-$C_4$)alkyl, hydroxyl, $C_1$-$C_2$ alkoxy, amino and (di)($C_1$-$C_2$)alkylamino groups;
aryl radicals optionally substituted with at least one radical chosen from ($C_1$-$C_4$)alkyl, hydroxyl, $C_1$-$C_2$ alkoxy, amino and (di)($C_1$-$C_2$)alkylamino radicals;
5- or 6-membered heteroaryl radicals, optionally substituted with at least one radical chosen from ($C_1$-$C_4$)alkyl and ($C_1$-$C_2$)alkoxy radicals;
$R_3$ and $R_4$ may also be a hydrogen atom;
$R_5$, $R_6$ and $R_7$, which may be identical or different, are chosen from:
hydrogen atoms;
linear and branched $C_1$-$C_4$ alkyl radicals optionally substituted with at least one radical chosen from hydroxyl, $C_1$-$C_2$ alkoxy, carboxamido $CONR_8R_9$, sulfonyl $SO_2R_8$ and aryl radicals optionally substituted with at least one radical chosen from ($C_1$-$C_4$)alkyl, hydroxyl, $C_1$-$C_2$ alkoxy, amino and (di)($C_1$-$C_2$)alkylamino radicals; aryl optionally substituted with at least one radical chosen from $(C_1-C_4)$alkyl, hydroxyl, $C_1-C_2$ alkoxy, amino and (di)$(C_1-C_2)$alkylamino radicals;

$R_6$ and $R_7$, which may be identical or different, may also be chosen from carboxamido radicals $CONR_8R_9$; and sulfonyl radicals $SO_2R_8$;

$R_8$ and $R_9$, which may be identical or different, are chosen from hydrogen atoms; linear and branched $C_1-C_4$ alkyl radicals optionally substituted with at least one radical chosen from hydroxyl radicals and $C_1-C_2$ alkoxy radicals;

$R_1$ and $R_2$, on the one hand, and $R_3$ and $R_4$, on the other hand, may form, with the nitrogen atom(s) to which they are attached, a saturated or unsaturated 5- to 7-membered heterocycle optionally substituted with at least one entity chosen from halogen atoms and amino, (di)$(C_1-C_4)$alkylamino, hydroxyl, carboxyl, carboxamido and $(C_1-C_2)$alkoxy radicals, and from $C_1-C_4$ alkyl radicals optionally substituted with at least one radical chosen from hydroxyl, amino, (di)alkylamino, alkoxy, carboxyl and sulfonyl radicals;

$R_3$ and $R_4$ may also form, together with the nitrogen atom to which they are attached, a 5- or 7-membered heterocycle, the carbon atoms of which may be replaced with an optionally substituted oxygen or nitrogen atom;

at least one coupler; and at least one associative polyurethane polymer.

\* \* \* \* \*